(12) United States Patent
Sheldon et al.

(10) Patent No.: US 9,629,736 B2
(45) Date of Patent: *Apr. 25, 2017

(54) SECURED STRAND END DEVICES

(71) Applicant: IDev Technologies, Inc., Webster, TX (US)

(72) Inventors: Jeffery Sheldon, League City, TX (US); Richard Booth, Friendswood, TX (US); Kenneth M. Bueche, Friendswood, TX (US)

(73) Assignee: IDev Technologies, Inc., Webster, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/331,667

(22) Filed: Oct. 21, 2016

(65) Prior Publication Data

US 2017/0035588 A1    Feb. 9, 2017

Related U.S. Application Data

(60) Continuation of application No. 15/229,844, filed on Aug. 5, 2016, which is a continuation of application No. 15/001,117, filed on Jan. 19, 2016, now Pat. No. 9,408,730, which is a continuation of application No. 14/601,152, filed on Jan. 20, 2015, now Pat. No.
(Continued)

(51) Int. Cl.
*A61F 2/90* (2013.01)

(52) U.S. Cl.
CPC ........ *A61F 2/90* (2013.01); *A61F 2220/0058* (2013.01)

(58) Field of Classification Search
CPC .... A61F 2/86; A61F 2/966; A61F 2/06; A61F 2002/061; A61F 2002/9665; A61F 2/95; A61F 2/90; A61F 2220/0058; A61F 2002/9534; D04C 1/06; D03D 41/00; D03D 3/02; D06C 7/00; Y10T 29/49849;
(Continued)

(56) References Cited

U.S. PATENT DOCUMENTS

| 619,403 A | 2/1899 | Grant et al. |
| 1,945,195 A | 1/1934 | Kellems |

(Continued)

FOREIGN PATENT DOCUMENTS

| AU | 10748/99 | 8/1999 |
| CA | 2083157 | 11/1991 |

(Continued)

OTHER PUBLICATIONS

Adam et al., "A New Design of the Esophageal Wallstent Endoprosthesis Resistant to Distal Migration," AJR, 170:1477-1481, Jun. 1998.
(Continued)

*Primary Examiner* — David Bryant
*Assistant Examiner* — Jun Yoo
(74) *Attorney, Agent, or Firm* — Knobbe Martens Olson & Bear LLP

(57) ABSTRACT

A woven, self-expanding stent device has one or more strands and is configured for insertion into an anatomical structure. The device includes a coupling structure secured to two different strand end portions that are substantially aligned with each other. The two different strand end portions include nickel and titanium. The coupling structure is not a strand of the device.

37 Claims, 11 Drawing Sheets

Related U.S. Application Data 9,408,729, which is a division of application No. 14/289,519, filed on May 28, 2014, now Pat. No. 8,966,733, which is a continuation of application No. 14/260,213, filed on Apr. 23, 2014, now Pat. No. 9,149,374, which is a division of application No. 13/549,334, filed on Jul. 13, 2012, now Pat. No. 8,739,382, which is a continuation of application No. 11/876,666, filed on Oct. 22, 2007.

(60) Provisional application No. 60/862,456, filed on Oct. 22, 2006.

(58) Field of Classification Search
CPC    B23K 2203/14; B23K 2201/32; B23K 26/20; D10B 2509/06
See application file for complete search history.

(56) References Cited

U.S. PATENT DOCUMENTS

| | | |
|---|---|---|
| 1,947,166 A | 2/1934 | Nydegger |
| 2,162,115 A | 6/1939 | Pauls |
| 2,836,181 A | 5/1958 | Tapp |
| 2,936,257 A | 5/1960 | Nailler et al. |
| 3,463,197 A | 8/1969 | Slade |
| 3,479,670 A | 11/1969 | Medell |
| 3,620,218 A | 11/1971 | Schmitt |
| 3,868,956 A | 3/1975 | Alfidi et al. |
| 4,003,289 A | 1/1977 | Yamashita |
| 4,081,885 A | 4/1978 | Shank |
| 4,418,693 A | 12/1983 | LaVeen et al. |
| 4,441,215 A | 4/1984 | Kaster |
| 4,469,101 A | 9/1984 | Coleman et al. |
| 4,503,569 A | 3/1985 | Dotter |
| 4,518,444 A | 5/1985 | Albrecht et al. |
| 4,567,917 A | 2/1986 | Millard |
| 4,580,568 A | 4/1986 | Gianturco |
| 4,619,246 A | 10/1986 | Molgaard-Nielsen et al. |
| 4,655,771 A | 4/1987 | Wallsten |
| 4,665,906 A | 5/1987 | Jervis |
| 4,728,328 A | 3/1988 | Hughes et al. |
| 4,733,665 A | 3/1988 | Palmaz |
| 4,739,762 A | 4/1988 | Palmaz |
| 4,768,507 A | 9/1988 | Fischell et al. |
| 4,771,773 A | 9/1988 | Kropf |
| 4,776,337 A | 10/1988 | Palmaz |
| 4,850,999 A | 7/1989 | Planck |
| 4,877,030 A | 10/1989 | Beck et al. |
| 4,893,543 A | 1/1990 | Phillips |
| 4,922,905 A | 5/1990 | Strecker |
| 4,950,227 A | 8/1990 | Savin et al. |
| 4,954,126 A | 9/1990 | Wallsten |
| 4,960,410 A | 10/1990 | Pinchuk |
| 4,969,458 A | 11/1990 | Wiktor |
| 4,990,151 A | 2/1991 | Wallsten |
| 4,992,905 A | 2/1991 | MacDougall et al. |
| 4,994,071 A | 2/1991 | MacGregor |
| 4,997,440 A | 3/1991 | Dumican |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,035,706 A | 7/1991 | Giantureo et al. |
| 5,059,211 A | 10/1991 | Stack et al. |
| 5,061,275 A | 10/1991 | Wallsten et al. |
| 5,064,435 A | 11/1991 | Porter |
| 5,067,957 A | 11/1991 | Jervis |
| 5,102,417 A | 4/1992 | Palmaz |
| 5,104,404 A | 4/1992 | Wolff |
| 5,107,852 A | 4/1992 | Davidson et al. |
| 5,116,365 A | 5/1992 | Hillstead |
| 5,133,732 A | 7/1992 | Wiktor |
| 5,135,536 A | 8/1992 | Hillstead |
| 5,159,920 A | 11/1992 | Condon et al. |
| 5,171,262 A | 12/1992 | MacGregor |
| 5,180,376 A | 1/1993 | Fischell |
| 5,190,546 A | 3/1993 | Jervis |
| 5,201,757 A | 4/1993 | Heyn et al. |
| 5,201,901 A | 4/1993 | Harada et al. |
| 5,211,658 A | 5/1993 | Clouse |
| 5,219,355 A | 6/1993 | Parodi et al. |
| 5,234,457 A | 8/1993 | Andersen |
| 5,246,445 A | 9/1993 | Yachia et al. |
| 5,256,158 A | 10/1993 | Tolkoff et al. |
| 5,261,916 A | 11/1993 | Engelson |
| 5,282,823 A | 2/1994 | Schwartz et al. |
| 5,282,824 A | 2/1994 | Giantruco |
| 5,304,220 A | 4/1994 | Maginot |
| 5,306,286 A | 4/1994 | Stack et al. |
| 5,342,387 A | 8/1994 | Summers |
| 5,350,398 A | 9/1994 | Pavcnik et al. |
| 5,360,443 A | 11/1994 | Barone et al. |
| 5,366,504 A | 11/1994 | Andersen et al. |
| 5,372,600 A | 12/1994 | Beyar et al. |
| 5,375,612 A | 12/1994 | Cottenceau et al. |
| 5,376,077 A | 12/1994 | Gomringer |
| 5,382,259 A | 1/1995 | Phelps et al. |
| 5,383,887 A | 1/1995 | Nadal |
| 5,383,925 A | 1/1995 | Schmitt |
| 5,389,106 A | 2/1995 | Tower |
| 5,391,172 A | 2/1995 | Williams et al. |
| 5,395,390 A | 3/1995 | Simon et al. |
| 5,405,377 A | 4/1995 | Cragg |
| 5,405,378 A | 4/1995 | Strecker |
| 5,411,507 A | 5/1995 | Heckele |
| 5,411,549 A | 5/1995 | Peters |
| 5,415,664 A | 5/1995 | Pinchuk |
| 5,419,231 A | 5/1995 | Earle, III et al. |
| D359,802 S | 6/1995 | Fontaine |
| 5,425,739 A | 6/1995 | Jessen |
| 5,425,984 A | 6/1995 | Kennedy et al. |
| 5,433,723 A | 7/1995 | Lindenberg et al. |
| 5,433,729 A | 7/1995 | Adams et al. |
| 5,443,496 A | 8/1995 | Schwartz et al. |
| 5,443,499 A | 8/1995 | Schmitt |
| 5,454,795 A | 10/1995 | Samson |
| 5,458,615 A | 10/1995 | Klemm et al. |
| 5,464,408 A | 11/1995 | Duc |
| 5,474,563 A | 12/1995 | Myler et al. |
| 5,476,508 A | 12/1995 | Amstrup |
| 5,478,355 A | 12/1995 | Muth et al. |
| 5,480,423 A | 1/1996 | Ravenscroft et al. |
| 5,484,425 A | 1/1996 | Fischell et al. |
| 5,484,444 A | 1/1996 | Braunschweiler et al. |
| 5,485,774 A | 1/1996 | Osborne |
| 5,496,277 A | 3/1996 | Termin et al. |
| 5,503,636 A | 4/1996 | Schmitt et al. |
| 5,507,769 A | 4/1996 | Marin et al. |
| 5,527,282 A | 6/1996 | Segal |
| 5,527,324 A | 6/1996 | Krantz et al. |
| 5,527,337 A | 6/1996 | Stack et al. |
| 5,534,007 A | 7/1996 | St. Germain et al. |
| 5,534,287 A | 7/1996 | Lukic |
| 5,536,274 A | 7/1996 | Neuss |
| 5,540,712 A | 7/1996 | Kleshinski et al. |
| 5,545,211 A | 8/1996 | An et al. |
| 5,551,954 A | 9/1996 | Buscemi et al. |
| 5,554,181 A | 9/1996 | Das |
| 5,562,725 A | 10/1996 | Schmitt et al. |
| 5,562,726 A | 10/1996 | Chuter |
| 5,571,167 A | 11/1996 | Maginot |
| 5,571,168 A | 11/1996 | Toro |
| 5,573,520 A | 11/1996 | Schwartz |
| 5,575,817 A | 11/1996 | Martin |
| 5,575,818 A | 11/1996 | Pinchuk |
| 5,591,172 A | 1/1997 | Bachmann et al. |
| 5,591,195 A | 1/1997 | Taheri et al. |
| 5,591,199 A | 1/1997 | Porter et al. |
| 5,591,222 A | 1/1997 | Susawa et al. |
| 5,591,226 A | 1/1997 | Trerotola et al. |
| 5,596,996 A | 1/1997 | Johanson et al. |
| 5,597,378 A | 1/1997 | Jervis |
| 5,601,593 A | 2/1997 | Freitag |

(56) References Cited

U.S. PATENT DOCUMENTS

| | | |
|---|---|---|
| 5,603,698 A | 2/1997 | Roberts et al. |
| 5,607,445 A | 3/1997 | Summers |
| 5,607,466 A | 3/1997 | Imbert et al. |
| 5,609,627 A | 3/1997 | Goicoechea et al. |
| 5,618,301 A | 4/1997 | Hauenstein et al. |
| 5,628,754 A | 5/1997 | Shevlin et al. |
| 5,628,787 A | 5/1997 | Mayer |
| 5,629,077 A | 5/1997 | Turnland et al. |
| 5,630,840 A | 5/1997 | Mayer |
| 5,632,771 A | 5/1997 | Boatman et al. |
| D380,831 S | 7/1997 | Kavteladze et al. |
| 5,643,339 A | 7/1997 | Kavteladze et al. |
| 5,645,532 A | 7/1997 | Horgan |
| 5,645,558 A | 7/1997 | Horton |
| 5,645,559 A | 7/1997 | Hachtman et al. |
| 5,651,533 A | 7/1997 | Ling |
| 5,653,684 A | 8/1997 | Laptewicz et al. |
| 5,653,727 A | 8/1997 | Wiktor |
| 5,662,703 A | 9/1997 | Yurek et al. |
| 5,662,713 A | 9/1997 | Andersen et al. |
| 5,665,115 A | 9/1997 | Cragg |
| 5,667,486 A | 9/1997 | Mikulich et al. |
| 5,667,523 A | 9/1997 | Bynon et al. |
| 5,669,880 A | 9/1997 | Solar |
| 5,669,924 A | 9/1997 | Shaknovich |
| 5,669,936 A | 9/1997 | Lazarus |
| 5,670,161 A | 9/1997 | Healy et al. |
| 5,674,241 A | 10/1997 | Bley et al. |
| 5,674,276 A | 10/1997 | Andersen et al. |
| 5,674,277 A | 10/1997 | Freitag |
| 5,679,400 A | 10/1997 | Tuch |
| 5,679,470 A | 10/1997 | Mayer |
| 5,683,411 A | 11/1997 | Kavteladze et al. |
| 5,683,448 A | 11/1997 | Cragg |
| 5,683,450 A | 11/1997 | Goicoechea et al. |
| 5,683,451 A | 11/1997 | Lenker et al. |
| 5,693,086 A | 12/1997 | Goicoechea et al. |
| 5,695,469 A | 12/1997 | Segal |
| 5,695,483 A | 12/1997 | Samson |
| 5,699,880 A | 12/1997 | Hockley |
| 5,700,269 A | 12/1997 | Pinchuk et al. |
| 5,700,285 A | 12/1997 | Myers et al. |
| 5,702,373 A | 12/1997 | Samson |
| 5,702,418 A | 12/1997 | Ravenscroft |
| 5,707,376 A | 1/1998 | Kavteladze et al. |
| 5,709,701 A | 1/1998 | Parodi |
| 5,709,703 A | 1/1998 | Lukic et al. |
| 5,713,917 A | 2/1998 | Leonhardt et al. |
| 5,713,948 A | 2/1998 | Uflacker |
| 5,716,365 A | 2/1998 | Goicoechea et al. |
| 5,716,396 A | 2/1998 | Williams, Jr. |
| 5,718,159 A | 2/1998 | Thompson |
| 5,718,724 A | 2/1998 | Goicoechea et al. |
| 5,720,735 A | 2/1998 | Dorros |
| 5,725,552 A | 3/1998 | Kotula et al. |
| 5,725,570 A | 3/1998 | Heath |
| 5,725,571 A | 3/1998 | Imbert et al. |
| 5,725,572 A | 3/1998 | Lam et al. |
| 5,728,150 A | 3/1998 | McDonald et al. |
| 5,728,158 A | 3/1998 | Lau et al. |
| 5,733,267 A | 3/1998 | Del Toro |
| 5,733,325 A | 3/1998 | Robinson et al. |
| 5,733,326 A | 3/1998 | Tomonto et al. |
| 5,733,327 A | 3/1998 | Igaki et al. |
| 5,735,892 A | 4/1998 | Myers et al. |
| 5,741,325 A | 4/1998 | Chaikof et al. |
| 5,741,333 A | 4/1998 | Frid |
| 5,749,880 A | 5/1998 | Banas et al. |
| 5,749,921 A | 5/1998 | Lenker et al. |
| 5,755,708 A | 5/1998 | Segal |
| 5,755,769 A | 5/1998 | Richard et al. |
| 5,758,562 A | 6/1998 | Thompson |
| 5,759,186 A | 6/1998 | Bachmann et al. |
| 5,766,204 A | 6/1998 | Porter et al. |
| 5,766,219 A | 6/1998 | Horton |
| 5,766,237 A | 6/1998 | Cragg |
| 5,766,710 A | 6/1998 | Turnlund et al. |
| 5,769,882 A | 6/1998 | Fogarty et al. |
| 5,772,668 A | 6/1998 | Summers et al. |
| 5,776,142 A | 7/1998 | Gunderson |
| 5,776,180 A | 7/1998 | Goicoechea et al. |
| 5,792,156 A | 8/1998 | Perouse |
| 5,797,952 A | 8/1998 | Klein |
| 5,800,508 A | 9/1998 | Goicoechea et al. |
| 5,800,511 A | 9/1998 | Mayer |
| 5,800,519 A | 9/1998 | Sandock |
| 5,807,398 A | 9/1998 | Shaknovich |
| 5,810,870 A | 9/1998 | Myers et al. |
| 5,817,102 A | 10/1998 | Johnson et al. |
| 5,817,126 A | 10/1998 | Imran |
| 5,824,034 A | 10/1998 | Schmitt et al. |
| 5,824,041 A | 10/1998 | Lenker et al. |
| 5,824,053 A | 10/1998 | Khosravi et al. |
| 5,824,058 A | 10/1998 | Ravenscroft et al. |
| 5,824,077 A | 10/1998 | Mayer |
| 5,830,229 A | 11/1998 | Kónya et al. |
| 5,836,966 A | 11/1998 | St. Germain |
| RE35,988 E | 12/1998 | Winston et al. |
| 5,843,158 A | 12/1998 | Lenker et al. |
| 5,843,168 A | 12/1998 | Dang |
| 5,843,176 A | 12/1998 | Weier |
| 5,849,037 A | 12/1998 | Frid |
| 5,851,217 A | 12/1998 | Wolff et al. |
| 5,851,228 A | 12/1998 | Pinheiro |
| 5,860,998 A | 1/1999 | Robinson et al. |
| 5,873,906 A | 2/1999 | Lau et al. |
| 5,876,386 A | 3/1999 | Samson |
| 5,876,432 A | 3/1999 | Lau et al. |
| 5,876,448 A | 3/1999 | Thompson et al. |
| 5,888,201 A | 3/1999 | Stinson et al. |
| 5,891,191 A | 4/1999 | Stinson |
| 5,902,332 A | 5/1999 | Schatz |
| 5,911,731 A | 6/1999 | Pham et al. |
| 5,913,896 A | 6/1999 | Boyle et al. |
| 5,916,196 A | 6/1999 | Andrea et al. |
| 5,916,263 A | 6/1999 | Goicocehea et al. |
| 5,919,224 A | 7/1999 | Thompson et al. |
| 5,925,074 A | 7/1999 | Gingras et al. |
| 5,928,279 A | 7/1999 | Shannon et al. |
| 5,928,280 A | 7/1999 | Hansen et al. |
| 5,931,842 A | 8/1999 | Goldsteen et al. |
| 5,938,696 A | 8/1999 | Goicoechea et al. |
| 5,941,908 A | 8/1999 | Goldsteen et al. |
| 5,944,738 A | 8/1999 | Amplatz et al. |
| 5,954,729 A | 9/1999 | Bachmann et al. |
| 5,954,764 A | 9/1999 | Parodi |
| 5,964,771 A | 10/1999 | Beyar et al. |
| 5,968,052 A | 10/1999 | Sullivan, III et al. |
| 5,968,070 A | 10/1999 | Bley et al. |
| 5,968,088 A | 10/1999 | Hansen et al. |
| 5,972,017 A | 10/1999 | Berg et al. |
| 5,972,441 A | 10/1999 | Campbell et al. |
| 5,976,155 A | 11/1999 | Foreman et al. |
| 5,976,178 A | 11/1999 | Goldsteen et al. |
| 5,984,877 A | 11/1999 | Fleischhacker, Jr. |
| 5,989,276 A | 11/1999 | Houser et al. |
| 6,000,601 A | 12/1999 | Walak |
| 6,004,348 A | 12/1999 | Banas et al. |
| 6,007,574 A | 12/1999 | Pulnev et al. |
| 6,010,530 A | 1/2000 | Goicoechea |
| 6,015,424 A | 1/2000 | Rosenbluth et al. |
| 6,017,319 A | 1/2000 | Jacobsen et al. |
| 6,019,778 A | 2/2000 | Wilson et al. |
| 6,019,785 A | 2/2000 | Strecker |
| 6,019,786 A | 2/2000 | Thompson |
| 6,019,789 A | 2/2000 | Dinh et al. |
| 6,024,763 A | 2/2000 | Lenker et al. |
| 6,027,528 A | 2/2000 | Tomonto et al. |
| 6,027,529 A | 2/2000 | Roychowdhury et al. |
| 6,036,702 A | 3/2000 | Bachinski et al. |
| 6,039,755 A | 3/2000 | Edwin et al. |
| 6,042,588 A | 3/2000 | Munsinger et al. |
| 6,042,589 A | 3/2000 | Marianne |
| 6,042,605 A | 3/2000 | Martin et al. |

(56) References Cited

U.S. PATENT DOCUMENTS

| | | |
|---|---|---|
| 6,048,338 A | 4/2000 | Larson et al. |
| 6,051,020 A | 4/2000 | Goicoechea et al. |
| 6,053,943 A | 4/2000 | Edwin et al. |
| 6,059,752 A | 5/2000 | Segal |
| 6,059,810 A | 5/2000 | Brown et al. |
| 6,059,825 A | 5/2000 | Hobbs et al. |
| 6,063,113 A | 5/2000 | Kavteladze et al. |
| 6,071,308 A | 6/2000 | Ballou et al. |
| 6,077,295 A | 6/2000 | Limon et al. |
| 6,080,191 A | 6/2000 | Summers |
| 6,090,115 A | 7/2000 | Beyar et al. |
| 6,090,125 A | 7/2000 | Horton |
| 6,102,890 A | 8/2000 | Stivland et al. |
| 6,102,932 A | 8/2000 | Kurz |
| 6,110,199 A | 8/2000 | Walak |
| 6,117,167 A | 9/2000 | Goicoechea et al. |
| 6,120,432 A | 9/2000 | Sullivan et al. |
| 6,120,522 A | 9/2000 | Vrba et al. |
| 6,123,115 A | 9/2000 | Greenhalgh |
| 6,123,723 A | 9/2000 | Konya et al. |
| 6,124,523 A | 9/2000 | Banas et al. |
| 6,126,685 A | 10/2000 | Lenker et al. |
| 6,136,006 A | 10/2000 | Johnson et al. |
| 6,136,007 A | 10/2000 | Goldsteen et al. |
| 6,142,975 A | 11/2000 | Jalisi et al. |
| 6,143,022 A | 11/2000 | Shull et al. |
| 6,146,403 A | 11/2000 | St. Germain |
| 6,146,415 A | 11/2000 | Fitz |
| 6,146,416 A | 11/2000 | Andersen et al. |
| 6,149,681 A | 11/2000 | Houser et al. |
| 6,152,945 A | 11/2000 | Bachinski et al. |
| 6,156,062 A | 12/2000 | McGuinness |
| 6,156,064 A | 12/2000 | Chouinard |
| 6,159,239 A | 12/2000 | Greenhalgh |
| 6,161,399 A | 12/2000 | Jayaraman |
| 6,162,244 A | 12/2000 | Braun et al. |
| 6,164,339 A | 12/2000 | Greenhalgh |
| 6,165,194 A | 12/2000 | Denardo |
| 6,165,210 A | 12/2000 | Lau et al. |
| 6,165,213 A | 12/2000 | Goicoechea et al. |
| 6,168,622 B1 | 1/2001 | Mazzocchi |
| 6,171,326 B1 | 1/2001 | Ferrera et al. |
| 6,172,617 B1 | 1/2001 | Bullock |
| 6,174,328 B1 | 1/2001 | Cragg |
| 6,174,329 B1 | 1/2001 | Callol et al. |
| 6,174,330 B1 | 1/2001 | Stinson |
| 6,183,508 B1 | 2/2001 | Stinson et al. |
| 6,186,942 B1 | 2/2001 | Sullivan et al. |
| 6,192,944 B1 | 2/2001 | Greenhalgh |
| 6,193,748 B1 | 2/2001 | Thompson et al. |
| 6,200,337 B1 | 3/2001 | Moriuchi et al. |
| 6,206,912 B1 | 3/2001 | Goldsteen et al. |
| 6,214,025 B1 | 4/2001 | Thistle et al. |
| 6,221,099 B1 | 4/2001 | Andersen et al. |
| 6,231,581 B1 | 5/2001 | Shank et al. |
| 6,237,460 B1 | 5/2001 | Frid |
| 6,238,402 B1 | 5/2001 | Sullivan, III et al. |
| 6,238,430 B1 | 5/2001 | Klumb et al. |
| 6,241,757 B1 | 6/2001 | An et al. |
| 6,245,103 B1 | 6/2001 | Stinson |
| 6,248,112 B1 | 6/2001 | Gambale et al. |
| 6,248,122 B1 | 6/2001 | Klumb et al. |
| 6,251,132 B1 | 6/2001 | Ravenscroft et al. |
| 6,251,135 B1 | 6/2001 | Stinson et al. |
| 6,258,080 B1 | 7/2001 | Samson |
| 6,261,315 B1 | 7/2001 | St. Germain et al. |
| 6,264,684 B1 | 7/2001 | Banas et al. |
| 6,264,689 B1 | 7/2001 | Colgan et al. |
| 6,270,521 B1 | 8/2001 | Fischell et al. |
| 6,280,467 B1 | 8/2001 | Leonhardt |
| 6,283,992 B1 | 9/2001 | Hankh et al. |
| 6,287,331 B1 | 9/2001 | Heath |
| 6,290,721 B1 | 9/2001 | Heath |
| 6,293,955 B1 | 9/2001 | Houser et al. |
| 6,293,965 B1 | 9/2001 | Berg et al. |
| 6,295,714 B1 | 10/2001 | Roychowdhury et al. |
| 6,296,622 B1 | 10/2001 | Kurz et al. |
| 6,299,636 B1 | 10/2001 | Schmitt et al. |
| 6,302,893 B1 | 10/2001 | Limon et al. |
| 6,302,905 B1 | 10/2001 | Goldsteen et al. |
| 6,302,906 B1 | 10/2001 | Goicoechea et al. |
| 6,306,105 B1 | 10/2001 | Rooney et al. |
| 6,306,141 B1 | 10/2001 | Jervis |
| 6,309,415 B1 | 10/2001 | Pulnev et al. |
| 6,312,454 B1 | 11/2001 | Stockel et al. |
| 6,319,267 B1 | 11/2001 | Kurz |
| 6,325,822 B1 | 12/2001 | Chouinard et al. |
| 6,329,069 B1 | 12/2001 | Azizi et al. |
| 6,331,184 B1 | 12/2001 | Abrams |
| 6,336,938 B1 | 1/2002 | Kavteladze et al. |
| 6,340,367 B1 | 1/2002 | Stinson et al. |
| 6,342,068 B1 | 1/2002 | Thompson |
| 6,346,118 B1 | 2/2002 | Baker et al. |
| 6,348,048 B1 | 2/2002 | Andrea et al. |
| 6,350,277 B1 | 2/2002 | Kocur |
| 6,350,278 B1 | 2/2002 | Lenker et al. |
| 6,352,531 B1 | 3/2002 | O'Connor et al. |
| 6,352,822 B1 | 3/2002 | Camp et al. |
| 6,355,060 B1 | 3/2002 | Lenker et al. |
| 6,355,070 B1 | 3/2002 | Andersen et al. |
| 6,361,637 B2 | 3/2002 | Martin et al. |
| 6,371,953 B1 | 4/2002 | Beyar et al. |
| 6,371,979 B1 | 4/2002 | Beyar et al. |
| 6,379,365 B1 | 4/2002 | Diaz |
| 6,379,392 B1 | 4/2002 | Walak |
| 6,383,214 B1 | 5/2002 | Banas et al. |
| 6,383,216 B1 | 5/2002 | Kavteladze et al. |
| 6,383,217 B1 | 5/2002 | Satz |
| 6,391,051 B2 | 5/2002 | Sullivan, III et al. |
| 6,398,802 B1 | 6/2002 | Yee |
| 6,398,803 B1 | 6/2002 | Layne et al. |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,541 B2 | 7/2002 | Denardo |
| 6,419,694 B1 | 7/2002 | Sandock |
| 6,423,084 B1 | 7/2002 | St. Germain |
| 6,423,085 B1 | 7/2002 | Murayama et al. |
| 6,425,898 B1 | 7/2002 | Wilson et al. |
| 6,440,161 B1 | 8/2002 | Madrid et al. |
| 6,447,522 B2 | 9/2002 | Gambale et al. |
| 6,451,025 B1 | 9/2002 | Jervis |
| 6,451,033 B1 | 9/2002 | Berg et al. |
| 6,451,047 B2 | 9/2002 | McCrea et al. |
| 6,451,052 B1 | 9/2002 | Burmeister et al. |
| 6,468,301 B1 | 10/2002 | Amplatz et al. |
| 6,468,303 B1 | 10/2002 | Amplatz et al. |
| 6,475,184 B1 | 11/2002 | Wang et al. |
| 6,475,209 B1 | 11/2002 | Larson et al. |
| 6,485,524 B2 | 11/2002 | Strecker |
| 6,488,700 B2 | 12/2002 | Klumb et al. |
| 6,488,705 B2 | 12/2002 | Schmitt et al. |
| 6,497,722 B1 | 12/2002 | Von Oepen et al. |
| 6,506,204 B2 | 1/2003 | Mazzocchi |
| 6,508,833 B2 | 1/2003 | Pavcnik et al. |
| 6,514,196 B1 | 2/2003 | Sullivan et al. |
| 6,514,261 B1 | 2/2003 | Randall et al. |
| 6,520,983 B1 | 2/2003 | Colgan et al. |
| 6,520,986 B2 | 2/2003 | Martin et al. |
| 6,527,802 B1 | 3/2003 | Mayer |
| 6,533,805 B1 | 3/2003 | Jervis |
| 6,533,810 B2 | 3/2003 | Hankh et al. |
| 6,547,819 B2 | 4/2003 | Strecker |
| 6,554,798 B1 | 4/2003 | Mann et al. |
| 6,558,414 B2 | 5/2003 | Layne |
| 6,559,312 B2 | 5/2003 | Krauss et al. |
| 6,562,064 B1 | 5/2003 | deBeer |
| 6,568,432 B2 | 5/2003 | Matsutani et al. |
| 6,572,645 B2 | 6/2003 | Leonhardt |
| 6,576,006 B2 | 6/2003 | Limon et al. |
| 6,579,314 B1 | 6/2003 | Lombardi et al. |
| 6,582,461 B1 | 6/2003 | Barmeister et al. |
| 6,585,695 B1 | 7/2003 | Adair et al. |
| 6,585,758 B1 | 7/2003 | Chouinard et al. |

(56) References Cited

U.S. PATENT DOCUMENTS

| | | |
|---|---|---|
| 6,592,614 B2 | 7/2003 | Lenker et al. |
| 6,592,617 B2 | 7/2003 | Thompson |
| 6,599,296 B1 | 7/2003 | Gillick et al. |
| 6,605,102 B1 | 8/2003 | Mazzocchi et al. |
| 6,607,551 B1 | 8/2003 | Sullivan et al. |
| 6,613,075 B1 | 9/2003 | Healy et al. |
| 6,622,604 B1 | 9/2003 | Chouinard et al. |
| 6,623,520 B2 | 9/2003 | Jalisi |
| 6,626,936 B2 | 9/2003 | Stinson |
| 6,629,981 B2 | 10/2003 | Bui et al. |
| 6,632,241 B1 | 10/2003 | Hancock et al. |
| 6,638,291 B1 | 10/2003 | Ferrera et al. |
| 6,641,608 B1 | 11/2003 | Pulnev et al. |
| 6,645,237 B2 | 11/2003 | Klumb et al. |
| 6,652,544 B2 | 11/2003 | Houser et al. |
| 6,652,574 B1 | 11/2003 | Jayaraman |
| 6,652,575 B2 | 11/2003 | Wang |
| 6,656,212 B2 | 12/2003 | Ravenscroft et al. |
| 6,656,218 B1 | 12/2003 | Denardo et al. |
| 6,660,030 B2 | 12/2003 | Shaolian et al. |
| 6,663,663 B2 | 12/2003 | Kim et al. |
| 6,673,883 B1 | 1/2004 | Rowan |
| 6,679,903 B2 | 1/2004 | Kurz |
| 6,685,738 B2 | 2/2004 | Chouinard et al. |
| 6,689,162 B1 | 2/2004 | Thompson |
| 6,695,862 B2 | 2/2004 | Cox et al. |
| 6,699,273 B2 | 3/2004 | Langan |
| 6,699,274 B2 | 3/2004 | Stinson |
| 6,702,829 B2 | 3/2004 | Bachinski et al. |
| 6,709,379 B1 | 3/2004 | Brandau et al. |
| 6,712,835 B2 | 3/2004 | Mazzochhi et al. |
| 6,719,934 B2 | 4/2004 | Stinson |
| 6,723,118 B1 | 4/2004 | Ballou et al. |
| 6,726,712 B1 | 4/2004 | Raeder-Devens et al. |
| 6,730,117 B1 | 5/2004 | Tseng et al. |
| 6,733,519 B2 | 5/2004 | Lashinski et al. |
| 6,736,839 B2 | 5/2004 | Cummings |
| 6,736,840 B2 | 5/2004 | Fischell et al. |
| 6,740,077 B1 | 5/2004 | Brandau et al. |
| 6,740,115 B2 | 5/2004 | Lombardi et al. |
| 6,743,219 B1 | 6/2004 | Dwyer et al. |
| 6,749,627 B2 | 6/2004 | Thompson et al. |
| 6,755,854 B2 | 6/2004 | Gillick et al. |
| 6,758,858 B2 | 7/2004 | McCrea et al. |
| 6,770,087 B2 | 8/2004 | Layne et al. |
| 6,773,446 B1 | 8/2004 | Dwyer et al. |
| 6,776,791 B1 | 8/2004 | Stallings et al. |
| 6,786,919 B1 | 9/2004 | Escano et al. |
| 6,786,920 B2 | 9/2004 | Shannon et al. |
| 6,790,218 B2 | 9/2004 | Jayaraman |
| 6,790,226 B2 | 9/2004 | Edwin et al. |
| 6,792,979 B2 | 9/2004 | Konya et al. |
| 6,797,217 B2 | 9/2004 | McCrea et al. |
| RE38,653 E | 11/2004 | Igaki et al. |
| 6,814,750 B2 | 11/2004 | Kavteladze et al. |
| 6,818,015 B2 | 11/2004 | Hankh et al. |
| 6,837,901 B2 | 1/2005 | Rabkin et al. |
| 6,846,316 B2 | 1/2005 | Abrams |
| 6,849,086 B2 | 2/2005 | Cragg |
| 6,855,155 B2 | 2/2005 | Denardo et al. |
| RE38,711 E | 3/2005 | Igaki et al. |
| 6,859,986 B2 | 3/2005 | Jackson et al. |
| 6,860,898 B2 | 3/2005 | Stack et al. |
| 6,863,685 B2 | 3/2005 | Davila et al. |
| 6,866,669 B2 | 3/2005 | Buzzard et al. |
| 6,866,679 B2 | 3/2005 | Kusleika |
| 6,872,011 B2 | 3/2005 | Ikeda et al. |
| 6,878,163 B2 | 4/2005 | Denardo et al. |
| 6,881,221 B2 | 4/2005 | Golds |
| 6,884,259 B2 | 4/2005 | Tran et al. |
| 6,913,618 B2 | 7/2005 | Denardo et al. |
| 6,918,882 B2 | 7/2005 | Skujins et al. |
| 6,926,732 B2 | 8/2005 | Derus et al. |
| 6,932,837 B2 | 8/2005 | Amplatz et al. |
| 6,939,352 B2 | 9/2005 | Buzzard et al. |
| 6,942,654 B1 | 9/2005 | Schaefer et al. |
| 6,942,682 B2 | 9/2005 | Vrba et al. |
| 6,942,688 B2 | 9/2005 | Bartholf et al. |
| 6,942,693 B2 | 9/2005 | Chouinard et al. |
| 6,949,103 B2 | 9/2005 | Mazzocchi et al. |
| 6,962,597 B2 | 11/2005 | Goodin |
| 6,974,472 B2 | 12/2005 | Hong et al. |
| 6,989,019 B2 | 1/2006 | Mazzocchi et al. |
| 6,989,024 B2 | 1/2006 | Hebert et al. |
| 6,997,945 B2 | 2/2006 | St. Germain |
| 6,997,948 B2 | 2/2006 | Stinson |
| 7,000,305 B2 | 2/2006 | Jayaraman |
| 7,001,420 B2 | 2/2006 | Speck et al. |
| 7,001,423 B2 | 2/2006 | Euteneuer et al. |
| 7,001,425 B2 | 2/2006 | McCullagh et al. |
| 7,011,675 B2 | 3/2006 | Hemerick et al. |
| 7,011,676 B2 | 3/2006 | Dong |
| 7,018,401 B1 | 3/2006 | Hyodoh et al. |
| 7,022,133 B2 | 4/2006 | Yee et al. |
| 7,033,375 B2 | 4/2006 | Mazzocchi et al. |
| 7,037,330 B1 | 5/2006 | Rivelli, Jr. et al. |
| 7,041,127 B2 | 5/2006 | Ledergerber |
| 7,048,014 B2 | 5/2006 | Hyodoh et al. |
| 7,048,752 B2 | 5/2006 | Mazzocchi et al. |
| 7,052,511 B2 | 5/2006 | Weldon et al. |
| 7,052,513 B2 | 5/2006 | Thompson |
| 7,060,150 B2 | 6/2006 | Banas et al. |
| 7,070,607 B2 | 7/2006 | Murayama et al. |
| 7,083,631 B2 | 8/2006 | Houser et al. |
| 7,083,640 B2 | 8/2006 | Lombardi et al. |
| 7,083,641 B2 | 8/2006 | Stinson et al. |
| 7,094,248 B2 | 8/2006 | Bachinski et al. |
| 7,105,016 B2 | 9/2006 | Shiu et al. |
| 7,115,141 B2 | 10/2006 | Menz et al. |
| 7,122,050 B2 | 10/2006 | Randall et al. |
| 7,137,993 B2 | 11/2006 | Acosta et al. |
| 7,147,618 B2 | 12/2006 | Kurz |
| 7,147,655 B2 | 12/2006 | Chermoni |
| 7,156,860 B2 | 1/2007 | Wallsten |
| 7,160,323 B2 | 1/2007 | Pulnev et al. |
| 7,172,617 B2 | 2/2007 | Colgan et al. |
| 7,175,650 B2 | 2/2007 | Ruetsch |
| 7,211,095 B2 | 5/2007 | Bachinski et al. |
| 7,211,109 B2 | 5/2007 | Thompson |
| 7,213,495 B2 | 5/2007 | McCullagh et al. |
| 7,235,096 B1 | 6/2007 | Van Tassel et al. |
| 7,241,308 B2 | 7/2007 | Andreas et al. |
| 7,264,631 B2 | 9/2007 | DiCarlo |
| 7,270,668 B2 | 9/2007 | Andreas et al. |
| 7,279,005 B2 | 10/2007 | Stinson |
| 7,288,112 B2 | 10/2007 | Denardo et al. |
| 7,306,756 B2 | 12/2007 | Edwin et al. |
| 7,309,349 B2 | 12/2007 | Jackson et al. |
| 7,311,031 B2 | 12/2007 | McCullagh et al. |
| 7,314,481 B2 | 1/2008 | Karpiel |
| 7,316,147 B2 | 1/2008 | Perreault et al. |
| 7,316,701 B2 | 1/2008 | Ferrera et al. |
| 7,316,708 B2 | 1/2008 | Gordon et al. |
| 7,320,702 B2 | 1/2008 | Hammersmark et al. |
| 7,326,236 B2 | 2/2008 | Andreas et al. |
| 7,329,279 B2 | 2/2008 | Haug et al. |
| 7,338,509 B2 | 3/2008 | Mattison |
| 7,344,514 B2 | 3/2008 | Shanley |
| 7,344,558 B2 | 3/2008 | Lorenzo et al. |
| 7,344,559 B2 | 3/2008 | Gray et al. |
| 7,367,985 B2 | 5/2008 | Mazzocchi et al. |
| 7,367,986 B2 | 5/2008 | Mazzocchi et al. |
| 7,367,987 B2 | 5/2008 | Balgobin et al. |
| 7,371,250 B2 | 5/2008 | Mazzocchi et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,381,219 B2 | 6/2008 | Salahieh et al. |
| 7,387,640 B2 | 6/2008 | Cummings |
| 7,396,362 B2 | 7/2008 | Jervis |
| 7,399,311 B2 | 7/2008 | Bertolino et al. |
| 7,399,314 B2 | 7/2008 | Butaric et al. |
| 7,402,170 B2 | 7/2008 | McCullagh et al. |
| 7,404,820 B2 | 7/2008 | Mazzocchi et al. |

(56) References Cited

U.S. PATENT DOCUMENTS

| | | |
|---|---|---|
| 7,410,492 B2 | 8/2008 | Mazzocchi et al. |
| 7,413,574 B2 | 8/2008 | Yip et al. |
| 7,419,502 B2 | 9/2008 | Pulnev et al. |
| 7,419,503 B2 | 9/2008 | Pulnev et al. |
| 7,442,200 B2 | 10/2008 | Mazzocchi et al. |
| 7,445,631 B2 | 11/2008 | Salahieh et al. |
| 7,455,739 B2 | 11/2008 | Zhou |
| 7,462,192 B2 | 12/2008 | Norton et al. |
| 7,468,071 B2 | 12/2008 | Edwin et al. |
| 7,485,130 B2 | 2/2009 | St. Germain |
| 7,491,224 B2 | 2/2009 | Cox et al. |
| 7,500,989 B2 | 3/2009 | Solem et al. |
| 7,510,570 B1 | 3/2009 | Goicoechea et al. |
| 7,517,361 B1 | 4/2009 | Ravenscroft |
| 7,520,893 B2 | 4/2009 | Rivelli, Jr. |
| 7,527,632 B2 | 5/2009 | Houghton et al. |
| 7,527,643 B2 | 5/2009 | Case et al. |
| 7,534,250 B2 | 5/2009 | Schaeffer et al. |
| RE40,816 E | 6/2009 | Taylor et al. |
| 7,550,001 B2 | 6/2009 | Dorn et al. |
| 7,550,002 B2 | 6/2009 | Goto et al. |
| 7,553,322 B2 | 6/2009 | Dorn et al. |
| 7,553,323 B1 | 6/2009 | Perez et al. |
| 7,556,635 B2 | 7/2009 | Mazzocchi et al. |
| 7,556,636 B2 | 7/2009 | Mazzocchi et al. |
| 7,566,338 B2 | 7/2009 | Mazzocchi et al. |
| 7,566,342 B2 | 7/2009 | Parker et al. |
| 7,572,273 B2 | 8/2009 | Mazzocchi et al. |
| 7,578,829 B2 | 8/2009 | Goldsteen et al. |
| 7,578,830 B2 | 8/2009 | Kusleika et al. |
| 7,578,838 B2 | 8/2009 | Melsheimer |
| 7,578,899 B2 | 8/2009 | Edwin et al. |
| 7,582,101 B2 | 9/2009 | Jones et al. |
| 7,582,108 B2 | 9/2009 | Hierlemann et al. |
| 7,588,597 B2 | 9/2009 | Frid |
| 7,594,928 B2 | 9/2009 | Headley, Jr. et al. |
| 7,604,661 B2 | 10/2009 | Pavcnik et al. |
| 7,608,058 B2 | 10/2009 | Wilson et al. |
| 7,608,099 B2 | 10/2009 | Johnson et al. |
| 7,611,528 B2 | 11/2009 | Goodson, IV et al. |
| 7,621,946 B2 | 11/2009 | Turner et al. |
| 7,628,803 B2 | 12/2009 | Pavcnik et al. |
| 7,628,806 B2 | 12/2009 | Yampolsky et al. |
| 7,637,934 B2 | 12/2009 | Mangiardi et al. |
| 7,651,521 B2 | 1/2010 | Ton et al. |
| 7,655,039 B2 | 2/2010 | Leanna et al. |
| 7,666,218 B2 | 2/2010 | Klein et al. |
| 7,670,355 B2 | 3/2010 | Mazzocchi et al. |
| 7,670,356 B2 | 3/2010 | Mazzocchi |
| 7,670,367 B1 | 3/2010 | Chouinard et al. |
| 7,678,130 B2 | 3/2010 | Mazzocchi et al. |
| 7,686,815 B2 | 3/2010 | Mazzocchi et al. |
| 7,691,124 B2 | 4/2010 | Balgobin |
| 7,695,506 B2 | 4/2010 | Thistle et al. |
| 7,695,507 B2 | 4/2010 | Rivelli, Jr. et al. |
| 7,717,923 B2 | 5/2010 | Kennedy, II et al. |
| 7,717,949 B2 | 5/2010 | Dorn |
| 7,736,386 B2 | 6/2010 | Pulnev et al. |
| 7,748,389 B2 | 7/2010 | Salahieh et al. |
| 7,749,244 B2 | 7/2010 | Bruckheimer et al. |
| 7,763,011 B2 | 7/2010 | Ortiz et al. |
| 7,763,068 B2 | 7/2010 | Pulnev et al. |
| 7,766,960 B2 | 8/2010 | Alexander et al. |
| 7,771,466 B2 | 8/2010 | Chouinard et al. |
| 7,780,720 B2 | 8/2010 | Goicoechea et al. |
| 7,785,340 B2 | 8/2010 | Heidner et al. |
| 7,789,903 B2 | 9/2010 | Spiridigliozzi et al. |
| 7,794,489 B2 | 9/2010 | Shumer et al. |
| 7,806,919 B2 | 10/2010 | Bloom et al. |
| 7,824,442 B2 | 11/2010 | Salahieh et al. |
| 7,824,443 B2 | 11/2010 | Salahieh et al. |
| 7,828,815 B2 | 11/2010 | Mazzocchi et al. |
| 7,828,816 B2 | 11/2010 | Mazzocchi et al. |
| 7,850,705 B2 | 12/2010 | Bachinski et al. |
| 7,850,724 B2 | 12/2010 | Oliver |
| 7,857,844 B2 | 12/2010 | Norton et al. |
| 7,867,268 B2 | 1/2011 | Shelso |
| 7,867,271 B2 | 1/2011 | Geiser et al. |
| 7,879,080 B2 | 2/2011 | Sato |
| 7,887,574 B2 | 2/2011 | McFerran |
| 7,901,449 B2 | 3/2011 | Goicoechea et al. |
| 7,918,880 B2 | 4/2011 | Austin |
| 7,922,732 B2 | 4/2011 | Mazzocchi et al. |
| 7,927,366 B2 | 4/2011 | Pulnev et al. |
| 7,935,140 B2 | 5/2011 | Griffin |
| 7,939,000 B2 | 5/2011 | McCrea et al. |
| 7,942,919 B2 | 5/2011 | Goicoechea et al. |
| 7,947,060 B2 | 5/2011 | Mazzocchi et al. |
| 7,959,666 B2 | 6/2011 | Salahieh et al. |
| 7,959,672 B2 | 6/2011 | Salahieh et al. |
| 7,963,987 B2 | 6/2011 | Melsheimer et al. |
| 8,052,739 B2 | 11/2011 | Pulnev et al. |
| 8,197,528 B2 | 6/2012 | Colgan et al. |
| 8,414,635 B2 | 4/2013 | Hyodoh et al. |
| 8,419,788 B2 | 4/2013 | Sheldon et al. |
| 8,671,815 B2 | 3/2014 | Hancock et al. |
| 8,739,382 B2 | 6/2014 | Sheldon et al. |
| 8,966,733 B2 | 3/2015 | Sheldon et al. |
| 9,149,374 B2 | 10/2015 | Sheldon et al. |
| 9,408,729 B2 | 8/2016 | Sheldon et al. |
| 9,408,730 B2 | 8/2016 | Sheldon et al. |
| 2001/0003801 A1 | 6/2001 | Strecker |
| 2001/0010007 A1 | 7/2001 | Bachinski et al. |
| 2001/0025131 A1 | 9/2001 | Edwin et al. |
| 2001/0032010 A1 | 10/2001 | Sandock |
| 2001/0049547 A1 | 12/2001 | Moore |
| 2001/0051809 A1 | 12/2001 | Houser et al. |
| 2002/0019659 A1 | 2/2002 | Goicoechea et al. |
| 2002/0022857 A1 | 2/2002 | Goldsteen et al. |
| 2002/0032477 A1 | 3/2002 | Helmus et al. |
| 2002/0055775 A1 | 5/2002 | Carpentier et al. |
| 2002/0087046 A1 | 7/2002 | Sullivan et al. |
| 2002/0087176 A1 | 7/2002 | Greenhalgh |
| 2002/0087181 A1 | 7/2002 | Goldsteen et al. |
| 2002/0138095 A1 | 9/2002 | Mazzocchi et al. |
| 2002/0147489 A1 | 10/2002 | Hong et al. |
| 2002/0151933 A1 | 10/2002 | Sheldon |
| 2002/0151955 A1 | 10/2002 | Tran et al. |
| 2002/0169474 A1 | 11/2002 | Kusleika |
| 2002/0173810 A1 | 11/2002 | Bachinski et al. |
| 2002/0173839 A1 | 11/2002 | Leopold et al. |
| 2003/0009215 A1 | 1/2003 | Mayer |
| 2003/0014062 A1 | 1/2003 | Houser et al. |
| 2003/0014063 A1 | 1/2003 | Houser et al. |
| 2003/0040771 A1 | 2/2003 | Hyodoh et al. |
| 2003/0040772 A1 | 2/2003 | Hyodoh et al. |
| 2003/0050686 A1 | 3/2003 | Raeder-Devens et al. |
| 2003/0083541 A1 | 5/2003 | Sullivan et al. |
| 2003/0100940 A1 | 5/2003 | Yodfat |
| 2003/0109886 A1 | 6/2003 | Keegan et al. |
| 2003/0130721 A1 | 7/2003 | Martin et al. |
| 2003/0153971 A1 | 8/2003 | Chandrasekaran |
| 2003/0208263 A1 | 11/2003 | Burmeister et al. |
| 2003/0216803 A1 | 11/2003 | Ledergerber |
| 2004/0024416 A1 | 2/2004 | Yodfat et al. |
| 2004/0039435 A1 | 2/2004 | Hancock et al. |
| 2004/0045645 A1 | 3/2004 | Zhou |
| 2004/0049262 A1 | 3/2004 | Obermiller et al. |
| 2004/0073287 A1 | 4/2004 | Goicoechea et al. |
| 2004/0093056 A1 | 5/2004 | Johnson et al. |
| 2004/0098081 A1 | 5/2004 | Landreville et al. |
| 2004/0098115 A1 | 5/2004 | Goicoechea et al. |
| 2004/0106979 A1 | 6/2004 | Goicoechea et al. |
| 2004/0117004 A1 | 6/2004 | Osborne et al. |
| 2004/0133264 A1 | 7/2004 | Moore |
| 2004/0186512 A1 | 9/2004 | Bruckheimer et al. |
| 2004/0186549 A1 | 9/2004 | Jayaraman |
| 2004/0193179 A1 | 9/2004 | Nikolchev |
| 2004/0199240 A1 | 10/2004 | Dorn |
| 2004/0215320 A1 | 10/2004 | Machek |
| 2004/0230286 A1 | 11/2004 | Moore et al. |
| 2004/0236402 A1 | 11/2004 | Layne et al. |
| 2004/0267348 A1 | 12/2004 | Gunderson et al. |
| 2005/0021123 A1 | 1/2005 | Dorn et al. |

(56) References Cited

U.S. PATENT DOCUMENTS

| | | |
|---|---|---|
| 2005/0049683 A1 | 3/2005 | Gray et al. |
| 2005/0049686 A1 | 3/2005 | Gray et al. |
| 2005/0059889 A1 | 3/2005 | Mayer |
| 2005/0080475 A1 | 4/2005 | Andreas et al. |
| 2005/0080480 A1 | 4/2005 | Bolea et al. |
| 2005/0085892 A1 | 4/2005 | Goto et al. |
| 2005/0090893 A1 | 4/2005 | Kavteladze et al. |
| 2005/0096733 A1 | 5/2005 | Kovneristy et al. |
| 2005/0119690 A1 | 6/2005 | Mazzochhi et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137699 A1 | 6/2005 | Salahieh et al. |
| 2005/0137701 A1 | 6/2005 | Salahieh et al. |
| 2005/0149171 A1 | 7/2005 | McCullagh et al. |
| 2005/0154439 A1 | 7/2005 | Gunderson |
| 2005/0163954 A1 | 7/2005 | Shaw |
| 2005/0182475 A1 | 8/2005 | Jen et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209676 A1 | 9/2005 | Kusleika |
| 2005/0256563 A1 | 11/2005 | Clerc et al. |
| 2005/0283168 A1 | 12/2005 | Gray |
| 2005/0283213 A1 | 12/2005 | Gray |
| 2005/0288751 A1 | 12/2005 | Gray |
| 2005/0288752 A1 | 12/2005 | Gray |
| 2005/0288764 A1 | 12/2005 | Snow et al. |
| 2006/0015168 A1 | 1/2006 | Gunderson |
| 2006/0036309 A1 | 2/2006 | Herbert et al. |
| 2006/0058835 A1 | 3/2006 | Murayama et al. |
| 2006/0058865 A1 | 3/2006 | Case |
| 2006/0058872 A1 | 3/2006 | Salahieh et al. |
| 2006/0074478 A1 | 4/2006 | Feller, III |
| 2006/0088654 A1 | 4/2006 | Ding et al. |
| 2006/0089705 A1 | 4/2006 | Ding et al. |
| 2006/0100687 A1 | 5/2006 | Fahey et al. |
| 2006/0116750 A1 | 6/2006 | Herbert et al. |
| 2006/0136034 A1 | 6/2006 | Modesitt et al. |
| 2006/0155363 A1 | 7/2006 | LaDuca et al. |
| 2006/0161195 A1 | 7/2006 | Goldsteen et al. |
| 2006/0184224 A1 | 8/2006 | Angel |
| 2006/0184238 A1 | 8/2006 | Kaufmann et al. |
| 2006/0190075 A1 | 8/2006 | Jordan et al. |
| 2006/0212105 A1 | 9/2006 | Dorn et al. |
| 2006/0229714 A1 | 10/2006 | Lombardi et al. |
| 2006/0241686 A1 | 10/2006 | Ferrera et al. |
| 2006/0253191 A1 | 11/2006 | Salahieh et al. |
| 2006/0271166 A1 | 11/2006 | Thill et al. |
| 2006/0276875 A1 | 12/2006 | Stinson et al. |
| 2006/0276887 A1 | 12/2006 | Brady et al. |
| 2007/0010876 A1 | 1/2007 | Salahieh et al. |
| 2007/0010877 A1 | 1/2007 | Salahieh et al. |
| 2007/0021821 A1 | 1/2007 | Johnson et al. |
| 2007/0043420 A1 | 2/2007 | Lostetter |
| 2007/0043430 A1 | 2/2007 | Stinson |
| 2007/0043433 A1 | 2/2007 | Chandrasekaran |
| 2007/0055299 A1 | 3/2007 | Ishimaru et al. |
| 2007/0055347 A1 | 3/2007 | Arbefeuille |
| 2007/0083253 A1 | 4/2007 | Fischell et al. |
| 2007/0093889 A1 | 4/2007 | Wu et al. |
| 2007/0100422 A1 | 5/2007 | Shumer et al. |
| 2007/0118206 A1 | 5/2007 | Colgan et al. |
| 2007/0118207 A1 | 5/2007 | Amplatz et al. |
| 2007/0118214 A1 | 5/2007 | Salahieh et al. |
| 2007/0156223 A1 | 7/2007 | Vaughan |
| 2007/0162103 A1 | 7/2007 | Case et al. |
| 2007/0162104 A1 | 7/2007 | Frid |
| 2007/0162107 A1 | 7/2007 | Haug et al. |
| 2007/0168018 A1 | 7/2007 | Amplatz et al. |
| 2007/0173927 A1 | 7/2007 | Shin et al. |
| 2007/0198076 A1 | 8/2007 | Hebert et al. |
| 2007/0203503 A1 | 8/2007 | Salahieh et al. |
| 2007/0203559 A1 | 8/2007 | Freudenthal et al. |
| 2007/0203563 A1 | 8/2007 | Hebert et al. |
| 2007/0208405 A1 | 9/2007 | Goodin et al. |
| 2007/0219612 A1 | 9/2007 | Andreas et al. |
| 2007/0219616 A1 | 9/2007 | Modesitt et al. |
| 2007/0219617 A1 | 9/2007 | Saint |
| 2007/0233224 A1 | 10/2007 | Leynov et al. |
| 2007/0244540 A1 | 10/2007 | Pryor |
| 2007/0244552 A1 | 10/2007 | Salahieh et al. |
| 2007/0250151 A1 | 10/2007 | Pereira |
| 2007/0255386 A1 | 11/2007 | Tenne |
| 2007/0265696 A1 | 11/2007 | Yu et al. |
| 2007/0270930 A1 | 11/2007 | Schenck |
| 2007/0270932 A1 | 11/2007 | Headley et al. |
| 2007/0270936 A1 | 11/2007 | Andreas et al. |
| 2007/0282420 A1 | 12/2007 | Gunderson |
| 2007/0293928 A1 | 12/2007 | Tomlin |
| 2007/0293929 A1 | 12/2007 | Aoba et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0004685 A1 | 1/2008 | Seemann et al. |
| 2008/0039863 A1 | 2/2008 | Keegan et al. |
| 2008/0091257 A1 | 4/2008 | Andreas et al. |
| 2008/0097572 A1 | 4/2008 | Sheldon et al. |
| 2008/0109059 A1 | 5/2008 | Gordon et al. |
| 2008/0125849 A1 | 5/2008 | Burpee et al. |
| 2008/0125859 A1 | 5/2008 | Salahieh et al. |
| 2008/0132989 A1 | 6/2008 | Snow et al. |
| 2008/0167709 A1 | 7/2008 | An |
| 2008/0183272 A1 | 7/2008 | Wood et al. |
| 2008/0221654 A1 | 9/2008 | Buiser et al. |
| 2008/0221670 A1 | 9/2008 | Clerc et al. |
| 2008/0221671 A1 | 9/2008 | Chouinard et al. |
| 2008/0234795 A1 | 9/2008 | Snow et al. |
| 2008/0234796 A1 | 9/2008 | Dorn |
| 2008/0234814 A1 | 9/2008 | Salahieh et al. |
| 2008/0262591 A1 | 10/2008 | Shin et al. |
| 2008/0288043 A1 | 11/2008 | Kaufmann et al. |
| 2008/0290076 A1 | 11/2008 | Sheldon et al. |
| 2008/0294231 A1 | 11/2008 | Aguilar et al. |
| 2008/0300667 A1 | 12/2008 | Hebert et al. |
| 2008/0300673 A1 | 12/2008 | Clerc et al. |
| 2008/0306580 A1 | 12/2008 | Jenson et al. |
| 2009/0005847 A1 | 1/2009 | Adams |
| 2009/0030495 A1 | 1/2009 | Koch |
| 2009/0036967 A1 | 2/2009 | Cummings |
| 2009/0043373 A1 | 2/2009 | Arnault De La Menardiere et al. |
| 2009/0054969 A1 | 2/2009 | Salahieh et al. |
| 2009/0054972 A1 | 2/2009 | Norton et al. |
| 2009/0082841 A1 | 3/2009 | Zacharias et al. |
| 2009/0099637 A1 | 4/2009 | Barthold et al. |
| 2009/0099643 A1 | 4/2009 | Hyodoh et al. |
| 2009/0112310 A1 | 4/2009 | Zhang |
| 2009/0138071 A1 | 5/2009 | Cheng et al. |
| 2009/0143849 A1 | 6/2009 | Ozawa et al. |
| 2009/0149936 A1 | 6/2009 | Lentz |
| 2009/0157158 A1 | 6/2009 | Ondracek et al. |
| 2009/0157162 A1 | 6/2009 | Chow et al. |
| 2009/0171442 A1 | 7/2009 | Young et al. |
| 2009/0177260 A1 | 7/2009 | Aggerholm |
| 2009/0177264 A1 | 7/2009 | Ravenscroft |
| 2009/0177268 A1 | 7/2009 | Lundkvist et al. |
| 2009/0182407 A1 | 7/2009 | Leanna et al. |
| 2009/0182410 A1 | 7/2009 | Case et al. |
| 2009/0198315 A1 | 8/2009 | Boudjemline |
| 2009/0214373 A1 | 8/2009 | Stinson et al. |
| 2009/0228092 A1 | 9/2009 | Raeder-Devens et al. |
| 2009/0234428 A1 | 9/2009 | Snow et al. |
| 2009/0234443 A1 | 9/2009 | Ottma et al. |
| 2009/0254168 A1 | 10/2009 | Parker et al. |
| 2009/0264985 A1 | 10/2009 | Bruszewski |
| 2009/0276028 A1 | 11/2009 | Bailey et al. |
| 2009/0276030 A1 | 11/2009 | Kusleika |
| 2009/0276033 A1 | 11/2009 | Mayer |

(56) References Cited

U.S. PATENT DOCUMENTS

| | | | |
|---|---|---|---|
| 2009/0287297 A1 | 11/2009 | Cox | |
| 2009/0299449 A1 | 12/2009 | Styrc | |
| 2009/0299451 A1 | 12/2009 | Ellsworth et al. | |
| 2009/0299461 A1 | 12/2009 | Chermoni | |
| 2009/0299464 A1 | 12/2009 | Cheng et al. | |
| 2009/0306762 A1 | 12/2009 | McCullagh et al. | |
| 2009/0311132 A1 | 12/2009 | Banas et al. | |
| 2009/0312829 A1 | 12/2009 | Aoba et al. | |
| 2009/0326636 A1 | 12/2009 | Hashimoto et al. | |
| 2009/0326637 A1 | 12/2009 | Hashimoto et al. | |
| 2010/0004726 A1 | 1/2010 | Hancock et al. | |
| 2010/0004729 A1 | 1/2010 | Chew et al. | |
| 2010/0004732 A1 | 1/2010 | Johnson et al. | |
| 2010/0010617 A1 | 1/2010 | Goodson, IV et al. | |
| 2010/0030320 A1 | 2/2010 | Feller, III | |
| 2010/0042198 A1 | 2/2010 | Burton | |
| 2010/0042199 A1 | 2/2010 | Burton | |
| 2010/0049291 A1 | 2/2010 | Yampolsky et al. | |
| 2010/0057191 A1 | 3/2010 | Pavcnik et al. | |
| 2010/0063582 A1 | 3/2010 | Rudakov | |
| 2010/0094399 A1 | 4/2010 | Dorn et al. | |
| 2010/0204774 A1 | 8/2010 | Goodin et al. | |
| 2010/0286756 A1 | 11/2010 | Dorn et al. | |
| 2011/0166643 A1 | 7/2011 | Pulnev et al. | |
| 2011/0295354 A1 | 12/2011 | Bueche et al. | |
| 2012/0330398 A1 | 12/2012 | Hyodoh et al. | |
| 2014/0114389 A1 | 4/2014 | Hyodoh et al. | |
| 2015/0148883 A1 | 5/2015 | Hyodoh et al. | |

FOREIGN PATENT DOCUMENTS

| | | | |
|---|---|---|---|
| CA | 2173644 | | 10/1996 |
| CA | 2173664 | | 10/1996 |
| CA | 2272947 | | 6/1998 |
| CA | 2007648 | C | 4/2000 |
| CA | 2247891 | | 7/2007 |
| CN | 1431920 | A | 7/2003 |
| DE | 3618734 | | 12/1986 |
| DE | 3713384 | | 10/1987 |
| DE | 3902364 | | 8/1989 |
| DE | 4022956 | | 2/1992 |
| DE | 4104702 | | 8/1992 |
| DE | 4235004 | | 4/1993 |
| DE | 4240177 | | 6/1994 |
| DE | 9390115 | | 12/1994 |
| DE | 4420142 | | 12/1995 |
| DE | 19531659 | | 3/1997 |
| DE | 68927998 | | 9/1997 |
| DE | 19703482 | | 8/1998 |
| DE | 29919625 | | 1/2000 |
| DE | 69131423 | | 1/2000 |
| DE | 19910188 | | 5/2000 |
| DE | 69427719 | | 10/2001 |
| DE | 102005020785 | | 11/2006 |
| DE | 102006053748 | | 4/2008 |
| EP | 0145166 | | 6/1985 |
| EP | 0518839 | | 12/1992 |
| EP | 0528039 | | 2/1993 |
| EP | 0622059 | | 11/1994 |
| EP | 0686379 | | 12/1995 |
| EP | 0689807 | | 1/1996 |
| EP | 0696447 | | 2/1996 |
| EP | 0701800 | | 3/1996 |
| EP | 0722700 | | 7/1996 |
| EP | 0737452 | | 10/1996 |
| EP | 0740928 | | 11/1996 |
| EP | 0743047 | | 11/1996 |
| EP | 0744163 | | 11/1996 |
| EP | 0744164 | | 11/1996 |
| EP | 0747021 | | 12/1996 |
| EP | 0782841 | | 7/1997 |
| EP | 0788012 | | 8/1997 |
| EP | 0788802 | | 8/1997 |
| EP | 0792627 | | 9/1997 |
| EP | 0804909 | | 11/1997 |
| EP | 0804934 | | 11/1997 |
| EP | 0812579 | | 12/1997 |
| EP | 0857471 | | 8/1998 |
| EP | 0857471 | A2 | 8/1998 |
| EP | 0864301 | | 9/1998 |
| EP | 0888758 | | 1/1999 |
| EP | 0891752 | | 1/1999 |
| EP | 0893108 | | 1/1999 |
| EP | 0759730 | B1 | 2/1999 |
| EP | 0894505 | | 2/1999 |
| EP | 0941716 | | 9/1999 |
| EP | 0943302 | | 9/1999 |
| EP | 0948946 | | 10/1999 |
| EP | 1010406 | | 6/2000 |
| EP | 1025813 | | 8/2000 |
| EP | 1121911 | | 8/2001 |
| EP | 1208816 | | 5/2002 |
| EP | 1221307 | | 7/2002 |
| EP | 1258229 | | 11/2002 |
| EP | 1275352 | | 1/2003 |
| EP | 1287790 | | 3/2003 |
| EP | 1396239 | | 3/2004 |
| EP | 1402847 | | 3/2004 |
| EP | 1447058 | | 8/2004 |
| EP | 1520557 | | 4/2005 |
| EP | 1582178 | | 10/2005 |
| EP | 1156757 | B1 | 12/2005 |
| EP | 1637092 | | 3/2006 |
| EP | 1803423 | | 7/2007 |
| EP | 1834610 | | 9/2007 |
| EP | 1844739 | | 10/2007 |
| EP | 1872742 | | 1/2008 |
| EP | 1900382 | | 3/2008 |
| EP | 1941845 | | 7/2008 |
| FR | 2678508 | | 1/1993 |
| FR | 2735967 | | 1/1997 |
| GB | 1183497 | | 3/1970 |
| GB | 1205743 | | 9/1970 |
| GB | 1565828 | | 4/1980 |
| GB | 2135585 | | 9/1984 |
| JP | 59-500652 | | 4/1984 |
| JP | S59-500652 | | 4/1984 |
| JP | H05-103830 | | 4/1993 |
| JP | H05-502179 | | 4/1993 |
| JP | 07-508199 | | 9/1995 |
| JP | H08-24346 | | 1/1996 |
| JP | 09-099095 | | 4/1997 |
| JP | H09-99095 | | 4/1997 |
| JP | 09-506540 | | 6/1997 |
| JP | 09-173469 | | 7/1997 |
| JP | 09-276302 | | 10/1997 |
| JP | 09-511160 | | 11/1997 |
| JP | 09-512460 | | 12/1997 |
| JP | H09-512460 | | 12/1997 |
| JP | 10-043313 | | 2/1998 |
| JP | 10-66730 | | 3/1998 |
| JP | H10-66730 | A | 3/1998 |
| JP | 10-272190 | | 10/1998 |
| JP | 11-57021 | | 3/1999 |
| JP | 2003-000722 | | 1/2003 |
| JP | 2003-088591 | | 3/2003 |
| JP | 2004-105381 | | 4/2004 |
| JP | 2004-510490 | | 4/2004 |
| JP | 2004-519307 | | 7/2004 |
| JP | 2004-344489 | | 9/2004 |
| JP | 2005-514155 | | 5/2005 |
| JP | 2002-535075 | | 10/2005 |
| JP | 2005-342539 | | 12/2005 |
| JP | 2006-506201 | | 2/2006 |
| JP | 2006-510393 | | 3/2006 |
| JP | 2006-522649 | | 5/2006 |
| JP | 2006-167458 | | 6/2006 |
| JP | 2008-519668 | | 6/2008 |
| RU | 1812980 | | 4/1993 |
| RU | 2012112203 | | 5/2006 |
| SU | 1457921 | | 2/1989 |
| WO | WO 83/03752 | | 11/1983 |
| WO | WO 87/04935 | | 8/1987 |
| WO | WO 89/03197 | | 4/1989 |

(56) References Cited

FOREIGN PATENT DOCUMENTS

| | | |
|---|---|---|
| WO | WO 90/05554 | 5/1990 |
| WO | WO 91/17789 | 11/1991 |
| WO | WO 92/13483 | 8/1992 |
| WO | WO 92/14408 | 9/1992 |
| WO | WO 92/15342 | 9/1992 |
| WO | WO 93/22986 | 11/1993 |
| WO | WO 94/00178 | 1/1994 |
| WO | WO 94/00179 | 1/1994 |
| WO | WO 94/03127 | 2/1994 |
| WO | WO 94/06372 | 3/1994 |
| WO | WO 94/16646 | 8/1994 |
| WO | WO 94/22379 | 10/1994 |
| WO | WO 94/27667 | 12/1994 |
| WO | WO 95/17859 | 7/1995 |
| WO | WO 95/21592 | 8/1995 |
| WO | WO 95/26775 | 10/1995 |
| WO | WO 95/27448 | 10/1995 |
| WO | WO 95/29646 | 11/1995 |
| WO | WO 95/31945 | 11/1995 |
| WO | WO 96/01591 | 1/1996 |
| WO | WO 96/17645 | 6/1996 |
| WO | WO 96/19953 | 7/1996 |
| WO | WO 96/28115 | 9/1996 |
| WO | WO 96/31174 | 10/1996 |
| WO | WO 96/32078 | 10/1996 |
| WO | WO 96/33677 | 10/1996 |
| WO | WO 96/40000 | 12/1996 |
| WO | WO 96/41589 | 12/1996 |
| WO | WO 97/09932 | 3/1997 |
| WO | WO 97/13475 | 4/1997 |
| WO | WO 97/16133 | 5/1997 |
| WO | WO 97/21401 | 6/1997 |
| WO | WO 97/21403 | 6/1997 |
| WO | WO 97/26939 | 7/1997 |
| WO | WO 97/32546 | 9/1997 |
| WO | WO 97/48343 | 12/1997 |
| WO | WO 98/11847 | 3/1998 |
| WO | WO 98/17435 | 4/1998 |
| WO | WO 98/19625 | 5/1998 |
| WO | WO 98/19629 | 5/1998 |
| WO | WO 98/19630 | 5/1998 |
| WO | WO 98/19636 | 5/1998 |
| WO | WO 98/23241 | 6/1998 |
| WO | WO 98/29043 | 7/1998 |
| WO | WO 98/33453 | 8/1998 |
| WO | WO 98/33454 | 8/1998 |
| WO | WO 98/39055 | 9/1998 |
| WO | WO 98/46168 | 10/1998 |
| WO | WO 98/52497 | 11/1998 |
| WO | WO 98/55027 | 12/1998 |
| WO | WO 99/04728 | 2/1999 |
| WO | WO 99/25271 | 5/1999 |
| WO | WO 99/32051 | 7/1999 |
| WO | WO 99/39646 | 8/1999 |
| WO | WO 99/44535 | 9/1999 |
| WO | WO 99/44538 | 9/1999 |
| WO | WO 99/49812 | 10/1999 |
| WO | WO 00/04845 | 2/2000 |
| WO | WO 00/09059 | 2/2000 |
| WO | WO 00/12016 | 3/2000 |
| WO | WO 00/17434 | 3/2000 |
| WO | WO 00/18330 | 4/2000 |
| WO | WO 00/25841 | 5/2000 |
| WO | WO 00/45741 | 8/2000 |
| WO | WO 00/45742 | 8/2000 |
| WO | WO 00/45743 | 8/2000 |
| WO | WO 00/48660 | 8/2000 |
| WO | WO 00/49973 | 8/2000 |
| WO | WO 00/71059 | 11/2000 |
| WO | WO 01/72240 | 10/2001 |
| WO | WO 01/93780 | 12/2001 |
| WO | WO 02/066091 | 8/2002 |
| WO | WO 02/081019 A1 | 10/2002 |
| WO | WO 02/087470 | 11/2002 |
| WO | WO 02/102279 | 12/2002 |
| WO | WO 03/003944 | 1/2003 |
| WO | WO 03/073963 | 9/2003 |
| WO | WO 03/075797 | 9/2003 |
| WO | WO 03/086239 | 10/2003 |
| WO | WO 2004/016201 A2 | 2/2004 |
| WO | WO 2004/045461 | 6/2004 |
| WO | WO 2004/080504 | 9/2004 |
| WO | WO 2004/084762 | 10/2004 |
| WO | WO 2004/091441 | 10/2004 |
| WO | WO 2005/062980 | 7/2005 |
| WO | WO 2006/010177 | 2/2006 |
| WO | WO 2006/053270 | 5/2006 |
| WO | WO 2006/088638 | 8/2006 |
| WO | WO 2008/027902 | 3/2008 |
| WO | WO 2008/063496 | 5/2008 |

OTHER PUBLICATIONS

Adam et al., Ed., Textbook of Metallic Stents, ISIS Medical Media, Oxford, pp. 108 and 216-221, 1997.

Ashley, The Ashley Book of Knots, pp. 191, 338, 537, 541, 343, 346 (1944).

Balko et al., "Transfemoral placement of intraluminal polyurethane prosthesis for abdominal aortic aneurysm," J. Surg. Res., 40:305-309, 1986.

Ben-Menachem et al., "Hemorrhage associated with pelvic fractures: causes, diagnosis, and emergent management," AJR, 157:1005-1014, 1991.

Bing et al., "Percutaneous ureteral occlusion with use of Gianturco coils and gelatin sponge, Part I. Swine model" JVIR; 3:313-317, 1992 (a).

Bing et al., "Percutaneous ureteral occlusion with use of Gianturco coils and gelatin sponge, Part II. Clinical Experience," JVIR; 3:319-321, 1992 (b).

Cambier et al., "Percutaneous closure of the small ((2.5 mm) patent ductus arteriosus using coil embolization," Am. J. Cardiol., 69:815-816, 1992.

Crochet et al., "Vena Tech-LGM filter: long-term results of a prospective study," Radiology, 188:857-860, 1993.

"Conformance by Design," World Medical Manufacturing Corporation, 1997.

Descriptions on poster presented at SCVIR 22nd Annual Scientific Meeting, Sheraton Washington Hotel, Mar. 8-13, 1997.

Didcott, "Oesophageal strictures: treatment by slow continuous dilation," Ann. Roy. Coll. Surg. Engl., 53:112-126, 1973.

Document entitled "Patient: #1115", faxed from Howard J. Leonhardt to András Kónya on Apr. 11, 1998.

Dorfman, "Percutaneous inferior vena cava filters," Radiology, 174:987-992, 1990.

Dotter, "Transluminally-placed coilspring endarterial tube grafts," Investigative Radiology, 4:329-332, 1969.

Dutton et al., "Pulmonary arteriovenous malformations: results of treatment with coil embolization in 53 patients," AJR, 165:1119-1125, 1995.

Fallone et al., "Elastic characteristics of the self-expanding metallic stents," Invest. Radiol., 23:370-376, 1988.

Fischell et al., "The β-particle-emitting radioisotope stent (Isostent): animal studies and planned clinical trials," Am. J. Cardiol., 78(Suppl 3A):45-50, 1996.

Furuse et al., "Hepatocellular carcinoma with portal vein tumor thrombus: embolization of arterioportal shunts," Radiology, 204:787-790, 1997.

Gianturco et al., "Mechanical devices for arterial occlusion," AJR, 124:428-435, 1975.

Gillams et al., "Self-expandable stainless steel braided endoprosthesis for biliary strictures," Radiology, 174:137-140, 1990.

Grassi, "Inferior vena caval filters: Analysis of five currently available devices," AJR, 156:813-821, 1991.

Grifka et al., "Transcatheter patent ductus arteriosus closure in an infant using the Gianturco-Grifka vascular occlusion device," Am. J. Cardiol., 78:721-723, 1996.

(56) References Cited

OTHER PUBLICATIONS

Guglielmi et al., "High-flow, small-hole arteriovenous fistulas: treatment with electrodetachable coils," AJNR, 16:325-328, 1995.
Günther et al., "Venous stenoses in dialysis shunts: Treatment with self-expanding metallic stents," Radiology, 170:401-405, 1989.
Hammer et al., "In vitro evaluation of vena cava filters," JVIR, 5:869-876, 1994.
Hendrickx et al., "Long-term survival after embolization of potentially lethal bleeding malignant pelvic tumors," Br. J. Radial., 68:1336-1343, 1995.
Hijazi et al., "Results of anterograde transcatheter closure of patent ductus arteriosus using single or multiple Gianturco coils," Am. J. Cardiol., 74:925-929, 1994.
Hijazi et al., "Transcatheter closure of patent ductus arteriosus using coils," Am. J. Cardiol., 79:1279-1280, 1997.
Hosking et al., "Transcatheter occlusion of the persistently patent ductus arteriosus," Circulation, 84:2313-2317, 1991.
How to Tie a Bow-Tie, www.cam.ac.uk/societies/cuhags/whitetie/howtotie.htm (3 pages) downloaded Jun. 17, 2011.
"How to Tie a Clove Hitch Knot," eHow, http://www.ehow.com/how_7532_tie-clove-hitch.html (3 pages) downloaded Jun. 17, 2011.
Hume et al., "Palliative use of a stent for colonic obstruction caused by adenocarcinoma in two cats," JAVMA, 228(3):392-396,2006.
Jaeger et al., "In vitro model for evaluation of inferior vena cava filters: effect of experimental parameters on thrombus-capturing efficacy of the Vena Tech-LGM filter," JVIR, 9:295-304, 1998.
JVIR Supplement, Scientific Program, SCVIR 22nd Annual Scientific Meeting, Mar. 8-13, 1997, Sheraton Washington Hotel, 8(1) Part 2, pp. 251-252, Jan.-Feb. 1997.
JVIR Supplement, vol. 10, No. 2, Part 2: 284, 287, Feb. 1999.
Kato et al., "Use of a self-expanding vascular occluder for embolization during endovascular aortic aneurysm repair," JVIR, 8:27-33, 1997.
Katsamouris et al., "Inferior vena cava filters: in vitro comparison of clot trapping and flow dynamics," Radiology, 166:361-366, 1988.
Korbin et al., "Comparison of filters in an oversized vena caval phantom: intracaval placement of a Bird's Nest filter versus biiliac placement of Greenfield, Vena Tech-LGM, and Simon nitinol filters," JVIR, 3:559-564, 1992.
Krichenko et al., "Angiographic classification of the isolated, persistently patent ductus arteriosus and implications for percutaneous catheter occlusion," Am. J. Cardiol., 63:877-880, 1989.
Kónya et al., "Anchoring coil embolization in a high-flow arterial model: A pilot study," JVIR, 9:249-254, 1998.
Kónya et al., "Endovascularly assembled aortic graft: A feasibility study," JVIR Supplement, 8(1) Part 2, pp. 251-252, Jan.-Feb. 1997.
Kónya et al., "Preliminary results with a new vascular basket occluder in swine," JVIR, 10:1043-1049, 1999.
Latson, "Residual shunts after transcatheter closure of patent ductus arteriosus," Circulation, 84:2591-2593, 1991.
Letter from Howard J. Leonhardt to Sidney Wallace, dated Apr. 22, 1997, with two attachments.
Levey et al., "Safety and efficacy of transcatheter embolization of auxiliary and shoulder arterial injuries," JVIR, 2:99-104, 1991.
Lipton et al., "Percutaneous Retrieval of two Wallstent endoprostheses from the heart through a single jugular sheath," JVIR, 6:469-472, 1995.
Lloyd et al., "Transcatheter occlusion of patent ductus arteriosus with Gianturco coils," Circulation, 88:1412-1420, 1993.
Magal et al., "A new device for transcatheter closure of patent ductus arteriosus: a feasibility study in dogs," Invest. Radiol., 24:272-276, 1989.
Marks et al., "A mechanically detachable coil for the treatment of aneurysms and occlusion of blood vessels," AJNR, 15:821-827, 1994.
Masura et al., "Catheter closure of moderate to large-sized patent ductus arteriosus using the new Amplatzer duct occluder: immediate and short-term results," J. Am. Coll. Cardiol., 31:878-882, 1998.

Millward, "Temporary and Retrievable inferior vena cava filters: Current status," JVIR, 9:381-387, 1998.
Milroy et al., "A new stent for the treatment of urethral strictures," Br. J. Urol., 63:392-396, 1989.
Murayama et al., "Nonadhesive liquid embolic agent for cerebral arteriovenous malformations: Preliminary histopathological studies in swine rete mirabile," Neurosurgery, 43(5):1164-1172, 1998.
Nancarrow et al., "Stability of coil emboli: an in vitro study," Cardiovasc. Intervent. Radiol., 10:226-229, 1987.
Nashef et al., "Expanding wire stents in benign tracheobronchial disease: Indications and complications," Ann. Thorac. Surg., 54:937-940, 1992.
O'Halpin et al., "Therapeutic arterial embolization: report of five years' experience," Clin. Radiol., 354:85-93, 1984.
Palmaz, "Balloon-expandable intravascular stent," AJR, 150:1263-1269, 1988.
Petersen et al., "Gianturco-Rösch Z stents in tracheobronchial stenoses," JVIR, 6:925-931, 1995.
Photograph taken by András Kónya of stent at SCVIR meeting in Orlando, Florida, Mar. 20-25, 1999.
Pictures of poster presented at SCVIR 22nd Annual Scientific Meeting, Sheraton Washington Hotel, Mar. 8-13, 1997.
Pozza et al., "Transcatheter occlusion of patent ductus arteriosus using a newly developed self-expanding device: evaluation in a canine model," Invest. Radiol., 30:104-109, 1995.
Prahlow et al., "Cardiac perforation due to Wallstent embolization: a fatal complication of the transjugular intrahepatic portosystemic shunt procedure," Radiology, 205:170-172, 1997.
Prince et al., "Local intravascular effects of the nitinol wire blood clot filter," Invest. Radiol., 23:294-300, 1988.
Punekar et al., "Post-surgical recurrent varicocele: efficacy of internal spermatic venography and steel-coil embolization," Br. J. Urol., 77:124-128, 1996.
Rashkind et al., "Nonsurgical closure of patent ductus arteriosus: clinical application of the Rashkind PDA occluder-system," Circulation, 75(3):583-592, 1987.
Reidy et al., "Interlocking detachable platinum coils, a controlled embolization device: early clinical experience," Cardiovasc. Intervent. Radiol., 19:85-90, 1996.
Sagara et al., "Recanalization after coil embolotherapy of pulmonary arteriovenous malformations: study of long-term outcome and mechanism for recanalization," AJR, 170:727-730, 1998.
Schampaert, "The V-stent: a novel technique for coronary bifurcation stenting," Cathet. Cardiovasc. Diagn., 39(3):320-326, 1996.
Schild et al., "Effectiveness of platinum wire microcoils for venous occlusion: a study on patients treated for venogenic impotence," Cardiovasc. Intervent. Radiol., 17:170-172, 1994.
Schmitz-Rode et al., "Self-expandable spindle for transcatheter vascular occlusion: in vivo experiments," Radiology, 188:95-100, 1993.
Schürmann et al., "Neointimal hyperplasia in low-profile nitinol stents, Palmaz stents, and Wallstents: a comparative experimental study," Cardiovasc. Intervent. Radiol. 19:248-254, 1996.
Schwartz et al., "Effectiveness of transcatheter embolization in the control of hepatic vascular injuries," JVIR, 4:359-365, 1993.
Selby Jr., "Interventional radiology of trauma," Radiol. Clin. N. Am., 30:427-439, 1992.
Seven photographs taken by Hideki Hyodoh of stents displayed during a Japanese metallic stentgraft meeting, Feb. 22, 1999.
Sharafuddin et al., "Experimental evaluation of a new self expanding patent ductus arteriosus occluder in a canine model," JVIR, 7:877-887, 1996.
Sharafuddin et al., "Repositionable vascular occluder: experimental comparison with standard Gianturco coils," JVIR, 7:695-703, 1996.
Simon et al., "Comparative evaluation of clinically available inferior vena cava filters with an in vitro physiologic simulation of the vena cava," Radiology, 189:769-774, 1993.
Sommer et al., "Use of preformed nitinol snare to improve transcatheter coil delivery in occlusion of patent ductus arteriosus," Am. J. Cardiol., 74:836-839, 1994.
Taki et al., "A new liquid material for embolization of arteriovenous malformations," AJNR, 11:163-168, 1990.

(56) References Cited

OTHER PUBLICATIONS

Teitelbaum et al., "Microcatheter embolization of non-neurologic traumatic vascular lesions," JVIR, 4:149-154, 1993.

Terada et al., "Embolization of arteriovenous malformations with peripheral aneurysms using ethylene vinyl alcohol copolymer," J. Neurosurg., 75:655-660, 1991.

Three photographs taken by András Kónya of poster authored by Hideki Hyodoh, András Kónya, and Kenneth C. Wright at SCVIR meeting in Orlando, Florida, Mar. 20-25, 1999.

Tometzki et al., "Transcatheter occlusion of the patent ductus arteriosus with Cook detachable coils," Heart, 76(6):531-535, 1996.

Uzun et al., "Transcatheter occlusion of the arterial duct with Cook detachable coils: early experience," Heart, 76(3):269-273, 1996.

Vedantham et al., "Uterine artery embolization: an underused method for controlling pelvic hemorrhage," Am. J. Obstet. Gynecol., 176(4):938-948, 1997.

Vesely et al., "Upper extremity central venous obstruction in hemodialysis patients: treatment with Wallstents," Radiology, 204:343-348, 1997.

Wallace et al., "Arterial occlusion of pelvic bone tumors," Cancer, 43: 322-328, 1979.

Wallace et al., "Tracheobronchial tree: Expandable metallic stents used in experimental and clinical applications," Radiology, 158:309-312, 1986.

"Wallstent Endoprosthesis" marketing material, Boston Scientific Vascular, 1998.

Weisse et al., "Evaluation of palliative stenting for management of malignant urethral obstructions in dogs," JAVMA, 229(2):226-234, 2006.

Wessel et al., "Outpatient closure of the patent ductus arteriosus," Circulation, 77(5):1068-1071, 1988.

White et al., "Pulmonary arteriovenous malformations: diagnosis and transcatheter embolotherapy," JVIR, 7:787-804, 1996.

White et al., "Pulmonary Arteriovenous Malformations: Techniques and Long-term Outcome of Embolotherapy," Radiology, 169:663-669, 1988.

World Medical News, 5(5), Feb. 1997.

World Medical News, 5(6), May 1997.

Xian et al., "Multiple emboli and filter function: An in vitro comparison of three vena cava filters," JVIR, 6:887-893, 1995.

Yune, "Inferior vena cava filter: Search for an ideal device," Radiology, 172:15-16, 1989.

Zarins et al., "AneuRx stent graft versus open surgical repair of abdominal aortic aneurysms: Multicenter prospective clinical trial," J. Vasc. Surg., 29:292-308, 1999.

Zubillaga et al., "Endovascular occlusion of intracranial aneurysms with electrically detachable coils: correlation of aneurysm neck size and treatment results," AJNR, 15:815-820, 1994.

| Stent Internal Dia. (mm) | Wire Dia. (in.) | Coupling Structure Length (in.) | Coupling Structure Internal Dia. (in.) | Coupling Structure External Dia. (in.) | Frequency (Hertz) | Peak Power (Watts) | Pulse Duration (milli-seconds) | A-scale (Lasag pulse compensation factor) | Argon Flow Rate (scfh) |
|---|---|---|---|---|---|---|---|---|---|
| 4.0000 | 0.0060 | 0.0700 | 0.0070 | 0.0090 | 10 | 200 | 0.25 | 120 | 5 |
| 5.0000 | 0.0060 | 0.0800 | 0.0070 | 0.0090 | 10 | 200 | 0.25 | 120 | 5 |
| 6.0000 | 0.0070 | 0.1000 | 0.0075 | 0.0105 | 10 | 200 | 0.30 | 100 | 5 |
| 7.0000 | 0.0070 | 0.1000 | 0.0075 | 0.0105 | 10 | 200 | 0.30 | 100 | 5 |
| 8.0000 | 0.0080 | 0.1200 | 0.0085 | 0.0120 | 10 | 200 | 0.30 | 100 | 5 |
| 9.0000 | 0.0080 | 0.1500 | 0.0085 | 0.0120 | 10 | 200 | 0.30 | 100 | 5 |
| 10.0000 | 0.0080 | 0.1500 | 0.0085 | 0.0120 | 10 | 200 | 0.30 | 100 | 5 |

| Internal Stent Dia. 0.5 (mm) | Stent Length (mm) | Nitinol Wire Dia. (in.) | Coupling Structure Code | A (in.) | B (in.) | C (in.) |
|---|---|---|---|---|---|---|
| 4.0 | 40 | 0.006 | -01 | 0.010 | 0.005 | 0.010 |
| 4.0 | 60 | 0.006 | -01 | 0.010 | 0.005 | 0.010 |
| 4.0 | 80 | 0.006 | -01 | 0.010 | 0.005 | 0.010 |
| 5.0 | 40 | 0.006 | -02 | 0.010 | 0.005 | 0.010 |
| 5.0 | 60 | 0.006 | -02 | 0.010 | 0.005 | 0.010 |
| 5.0 | 80 | 0.006 | -02 | 0.010 | 0.005 | 0.010 |
| 5.0 | 100 | 0.006 | -02 | 0.010 | 0.005 | 0.010 |
| 5.0 | 120 | 0.006 | -02 | 0.010 | 0.005 | 0.010 |
| 6.0 | 40 | 0.007 | -03 | 0.015 | 0.008 | 0.010 |
| 6.0 | 60 | 0.007 | -03 | 0.015 | 0.008 | 0.010 |
| 6.0 | 80 | 0.007 | -03 | 0.015 | 0.008 | 0.010 |
| 6.0 | 100 | 0.007 | -03 | 0.015 | 0.008 | 0.010 |
| 6.0 | 120 | 0.007 | -03 | 0.015 | 0.008 | 0.010 |
| 7.0 | 40 | 0.007 | -03 | 0.015 | 0.008 | 0.010 |
| 7.0 | 60 | 0.007 | -03 | 0.015 | 0.008 | 0.010 |
| 7.0 | 80 | 0.007 | -03 | 0.015 | 0.008 | 0.010 |
| 7.0 | 100 | 0.007 | -03 | 0.015 | 0.008 | 0.010 |
| 7.0 | 120 | 0.007 | -03 | 0.015 | 0.008 | 0.010 |
| 8.0 | 40 | 0.008 | -04 | 0.015 | 0.008 | 0.010 |
| 8.0 | 60 | 0.008 | -04 | 0.015 | 0.008 | 0.010 |
| 8.0 | 80 | 0.008 | -04 | 0.015 | 0.008 | 0.010 |
| 8.0 | 100 | 0.008 | -04 | 0.015 | 0.008 | 0.010 |
| 8.0 | 120 | 0.008 | -04 | 0.015 | 0.008 | 0.010 |
| 9.0 | 40 | 0.008 | -05 | 0.020 | 0.008 | 0.010 |
| 9.0 | 60 | 0.008 | -05 | 0.020 | 0.008 | 0.010 |
| 10.0 | 40 | 0.008 | -05 | 0.020 | 0.008 | 0.010 |
| 10.0 | 60 | 0.008 | -05 | 0.020 | 0.008 | 0.010 |
| 5.0 | 150 | 0.006 | -02 | 0.010 | 0.005 | 0.010 |
| 6.0 | 150 | 0.007 | -03 | 0.015 | 0.008 | 0.010 |
| 7.0 | 150 | 0.007 | -03 | 0.015 | 0.008 | 0.010 |

*FIG. 14B*

SECURED STRAND END DEVICES

CROSS-REFERENCE(S) TO RELATED APPLICATION(S)

This application is a continuation of U.S. application Ser. No. 15/229,844, filed Aug. 5, 2016, which is a continuation of U.S. application Ser. No. 15/001,117, now U.S. Pat. No. 9,408,730, filed Jan. 19, 2016, which is a continuation of U.S. application Ser. No. 14/601,152, now U.S. Pat. No. 9,408,729, filed Jan. 20, 2015, which is a divisional of U.S. application Ser. No. 14/289,519, now U.S. Pat. No. 8,966,733, which was filed May 28, 2014, which is a continuation of Ser. No. 14/260,213, now U.S. Pat. No. 9,149,374, which was filed Apr. 23, 2014, which is a divisional of U.S. application Ser. No. 13/549,334, now U.S. Pat. No. 8,739,382, which was filed Jul. 13, 2012, which is a continuation of U.S. patent application Ser. No. 11/876,666, which was filed on Oct. 22, 2007, which claims priority benefit of U.S. Provisional Application App. Ser. No. 60/862,456, filed Oct. 22, 2006, all of which applications are hereby incorporated by reference in their entirety.

BACKGROUND

1. Field

The present invention relates generally techniques and structures for securing the ends of strands, such as wires, of devices suited for placement in anatomical structures, and the resulting devices. Examples of such devices include woven, self-expanding stents.

2. Description of Related Art

Examples of devices suitable for insertion into an anatomical structure that are created from one or more strands are found in U.S. Pat. Nos. 6,007,574; 6,419,694; and 7,018,401; and in U.S. Patent Application Publication Nos. US 2005/0049682 and US 2006/0116752, all of which are incorporated by reference.

SUMMARY OF THE INVENTION

Some embodiments of the present methods include securing a coupling structure to a first strand end portion of a device configured for insertion into an anatomical structure; and securing the coupling structure to a second strand end portion of the device; where the first and second strand end portions are substantially aligned, the coupling structure is not a strand of the device, and the device includes one or more strands that include nickel and titanium. In some embodiments, the length of the coupling structure is less than 25, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 percent of the length of the device; this may be true for each coupling structure that is used. The coupling structure may be configured such that it has a passageway before it is secured to the first and second strand portions, and it may be placed into direct contact with the first and second strand end portions prior to the securing. The device may be a stent (e.g., a stent woven from multiple strands), or any other medical device suited for use in treating a patient, such as a filter or an occluder. The device may be self-expanding. The device may have two or more device ends (such as the two ends of a straight stent or the three ends of a bifurcated stent), and each device end may be characterized by or defined by strand bends, where the strand bends of a given device end are similar (e.g., substantially similar) in shape to at least each other and in some instances to all of the strand bends of all the device ends, such that one device end looks very similar to the other device end or device ends. The number of coupling structures that are used may correspond to the number of strands (e.g., wires) that are used to create the device, and they may be positioned in axial alignment (parallel to the longitudinal axis of the device) or they may be axially offset from each other and positioned around the circumference of the device. The securing may be accomplished by welding (e.g., laser welding) the coupling structure to the first strand end portion to create a first welded region and by welding the coupling structure to the second strand end portion to create a second welded region. The two welded regions may be separated from each and unconnected by any other welded region. The two strand end portions directly touch each other in some embodiments, and in other embodiments are not in direct contact with each other. The strand end portions may be substantially aligned with each other (end-to-end), or they may be positioned in side-by-side relationship (which may be characterized as overlapping). In some embodiments, the coupling structure is a piece of material that is separate from the first strand end portion and from the second strand end portion and, when a weld is used to accomplish the securing, is placed into direct contact with both strand end portions before the welding begins. In some embodiments, some or all of the securing steps result in a given half of a given strand being secured to either (a) only one other strand or (b) only the other half of the same strand. In some embodiments, the coupling structure is positioned beneath a strand that crosses over it. In some embodiments, all coupling structures that are used are positioned in this same fashion. In some embodiments, neither the coupling structure nor the strand end portions to which it is secured undergo a smoothing step after the securing is complete. In some embodiments where the device is woven from multiple strands such that strand crossings are created defining obtuse angles that increase when the device is axially compressed from an unconstrained state, each device opening (other than the openings that border the longitudinal passageway or passageways of the device) is defined by at least three strand crossings, where each strand crossing is defined by two crossed strand portions. In some embodiments, the coupling structure positioned nearest to a particular end of the device (a "device end") is spaced apart from all device ends (even at the portion of the coupling structure nearest the device end in question) by at least one strand crossing (in some embodiments, by at least two strand crossings; in some embodiments, by at least three strand crossings; in some embodiments, by at least four strand crossing; in some embodiments, by at least five strand crossings) in a direction (e.g., along a line) that is substantially parallel with a longitudinal axis of the device.

Some embodiments of the present methods include welding a coupling structure to a first strand end portion of a device configured for insertion into an anatomical structure; and welding the coupling structure to a second strand end portion of the device; where the coupling structure is not a strand of the device, and the device includes one or more strands that include nickel and titanium.

The present devices may have one or more strands and be configured for insertion into an anatomical structure. In some embodiments, the present devices include a coupling structure secured to two different strand end portions that are substantially aligned with each other; where the two different strand end portion includes nickel and titanium, and the coupling structure is not a strand of the device. In some embodiments, the present devices include a coupling structure welded to two different strand end portions; where the two different strand end portion includes nickel and titanium, and the coupling structure is not a strand of the device. The device may be a stent, or any other medical device suited for use in treating a patient, such as a filter or an occluder. The number of coupling structures that are used may correspond to the number of strands (e.g., wires) the device has, and they may be positioned in axial alignment (parallel to the longitudinal axis of the woven device) or they may be axially offset from each other and positioned around the circumference of the device. The strand end portions in each pair that are secured with (e.g., welded to) a given coupling structure may be substantially aligned with each other or they may be placed in side-by-side relationship with each other (which may be characterized as overlapping). In some embodiments, the length of the coupling structure is less than 25, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 percent of the length of the device; this may be true for each coupling structure that is used. The coupling structure may be configured such that it has a passageway before it is secured to the first and second strand portions, and it may be placed into direct contact with the first and second strand end portions prior to being secured (e.g., welded). The device may be a stent (e.g., a stent woven from multiple strands), or any other medical device suited for use in treating a patient, such as a filter or an occluder. The device may be self-expanding. The device may have two or more device ends (such as the two ends of a straight stent or the three ends of a bifurcated stent), and each device end may be characterized by or defined by strand bends, where the strand bends of a given device end are similar (e.g., substantially similar) in shape to at least each other and in some instances to all of the strand bends of all the device ends, such that one device end looks very similar to the other device end or device ends. The number of coupling structures that are used may correspond to the number of strands (e.g., wires) that are used to create the device, and they may be positioned in axial alignment (parallel to the longitudinal axis of the device) or they may be axially offset from each other and positioned around the circumference of the device. The coupling structure may be secured to the first strand end portion by a weld that forms a first welded region, the coupling structure is secured to the second strand end portion by a weld that forms a second welded region, and the first and second welded regions are not directly connected to each other by another welded region. The two welded regions may be separated from each and unconnected by any other welded region. The two strand end portions directly touch each other in some embodiments, and in other embodiments are not in direct contact with each other. In some embodiments, the coupling structure is a piece of material that is separate from the first strand end portion and from the second strand end portion and, when a weld is used to secure the coupling structure to those strand end portions, is placed into direct contact with both strand end portions before the welding begins. In some embodiments, a given half of a given strand of the device is secured to either (a) only one other strand or (b) only the other half of the same strand. In some embodiments, the coupling structure is positioned beneath a strand that crosses over it. In some embodiments, all coupling structures that are used are positioned in this same fashion. In some embodiments, neither the coupling structure nor the strand end portions to which it is secured require smoothing after being secured. In some embodiments where the device is woven from multiple strands such that strand crossings are created defining obtuse angles that increase when the device is axially compressed from an unconstrained state, each device opening (other than the openings that border the longitudinal passageway or passageways of the device) is defined by at least three strand crossings, where each strand crossing is defined by two crossed strand portions. In some embodiments, the coupling structure positioned nearest to a particular end of the device (a "device end") is spaced apart from all device ends (even at the portion of the coupling structure nearest the device end in question) by at least one strand crossing (in some embodiments, by at least two strand crossings; in some embodiments, by at least three strand crossings; in some embodiments, by at least four strand crossing; in some embodiments, by at least five strand crossings) in a direction (e.g., along a line) that is substantially parallel with a longitudinal axis of the device.

Details associated with these embodiments and others are provided below.

BRIEF DESCRIPTION OF THE DRAWINGS

The following drawings illustrate by way of example and not limitation. Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear.

FIG. 14B is a table containing example values for the dimensions depicted in FIG. 14A and other aspects of a stent created according to the present methods.

DESCRIPTION OF ILLUSTRATIVE EMBODIMENTS

Figure 1:
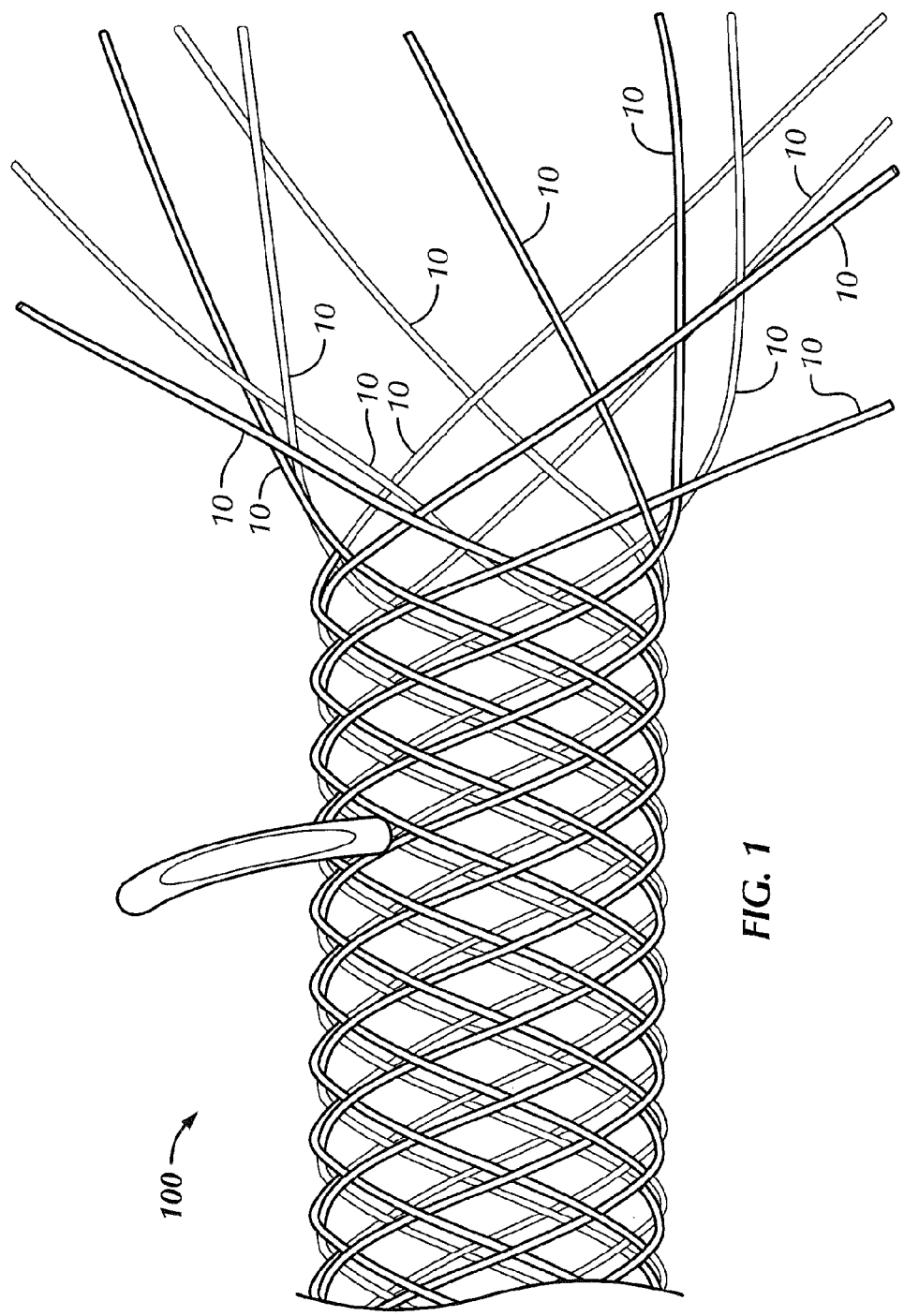
FIG. 1 shows an example of a portion of a device that is being configured for insertion into an anatomical structure, and at a stage of creation where free strand ends are positioned at one end of the device. There is a hook depicted in the top, central portion of the figure that is holding the device to an underlying surface. The hook is not part of the device.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or method that "comprises," "has," "contains," or "includes" one or more elements possesses those one or more elements, but is not limited to possessing only those one or more elements or steps. Likewise, an element of a device or a step of a method that "comprises," "has," "contains," or "includes" one or more features possesses those one or more features, but is not limited to possessing only those one or more features. Furthermore, a structure that is configured in a certain way must be configured in at least that way, but also may be configured in a way or ways that are not specified.

Any embodiment of any of the present methods and devices may consist of or consist essentially of—rather than comprise/include/contain/have—the described steps and/or features. Thus, and by way of example, while some embodiments of the present methods comprise welding a coupling structure to a first strand end portion of a device configured for insertion into an anatomical structure; and welding the coupling structure to a second strand end portion of the device; where the coupling structure is not a strand of the device, and the device includes one or more strands that include nickel and titanium, other embodiments consist essentially of or consist of welding a coupling structure to a first strand end portion of a device configured for insertion into an anatomical structure; and welding the coupling structure to a second strand end portion of the device; where the coupling structure is not a strand of the device, and the device includes one or more strands that include nickel and titanium.

The terms "a" and "an" are defined as one or more than one unless this disclosure explicitly requires otherwise. The terms "substantially" and "about" are defined as at least close to (and include) a given value or state (preferably within 10% of, more preferably within 1% of, and most preferably within 0.1% of).

The present methods may be used to secure two unsecured strand ends of a device configured for insertion into an anatomical structure. The initial process used to create the device may involve weaving—such as the weaving techniques disclosed in U.S. Pat. Nos. 6,792,979 and 7,048,014, which are incorporated by reference—or any other process that results in at least two unsecured strand ends. If weaving is used, one suitable braiding machine that may be used is the Steeger 24 Carrier Horizontal Fine Wire Carrier Braider HS 140-24-IH manufactured by Steeger USA (Spartanburg, S.C.). The device may be created from one or more strands, and it may have a variety of configurations, such as stent (e.g., one with two ends or a multi-legged stent with more than two ends), an occluder, or a filter. The strand ends may be secured with a coupling structure that includes a passageway (such as a small tube) into which the strand ends can be inserted from opposite ends and that is welded (e.g., laser welded) to the strand end portions inserted into it. However, the coupling structure need not encompass the strand ends, as a small tube does. Instead, in other embodiments, the coupling structure could comprise a flat strip to which the strand ends are coupled, or a strip that is contoured, such as a portion of a small tube. Furthermore, though laser welding is discussed below as a preferred joining technique, other techniques may be used, including (but not limited to) electron beam welding, resistance welding, tungsten inert gas welding, metal inert gas welding, crimping, soldering, braising, and gluing.

The coupling structure may be made from the same materials as the strand end portions to which it is coupled (e.g., a nickel-titanium coupling structure may be used to couple two nickel-titanium strand end portions together), or it may be made from a different material or materials (e.g., a stainless steel coupling structure may be used to couple two nickel-titanium strand end portions together).

In embodiments in which is woven from nickel-titanium wires (nickel—56.0 percent by weight of the total composition; titanium—balance of the total composition), and the initial weaving is complete, the device (with the mandrel on which it was formed, if desired) can be heat treated according to the information in Table 1 below:

TABLE 1

| Stent Diameter (mm) | Furnace Temperature Setting (° C.) | Heat Treatment Time (minutes) |
| --- | --- | --- |
| 4.0 | 525 | 5 |
| 5.0 | 535 | 5 |
| 6.0 | 510 | 10 |
| 7.0 | 520 | 10 |
| 8.0 | 510 | 13 |
| 9.0 | 520 | 13 |
| 10.0 | 530 | 13 |

The device may have free strand ends positioned at some or all of the ends of the device when it is heat treated in this fashion. FIG. 1 shows an example of a device (device 100) that has one or more strands and is configured for insertion into an anatomical structure. Device 100, which is a stent, was created woven according to techniques disclosed in U.S. Pat. No. 7,018,401 from six strands (wires) that possess twelve strand halves 10. There are no free strand ends at the device end of device 100 that is not shown. Each half strand was secured (see, e.g., FIG. 3) to only one other half strand (which either belonged to the same or a different strand).

Figure 2:
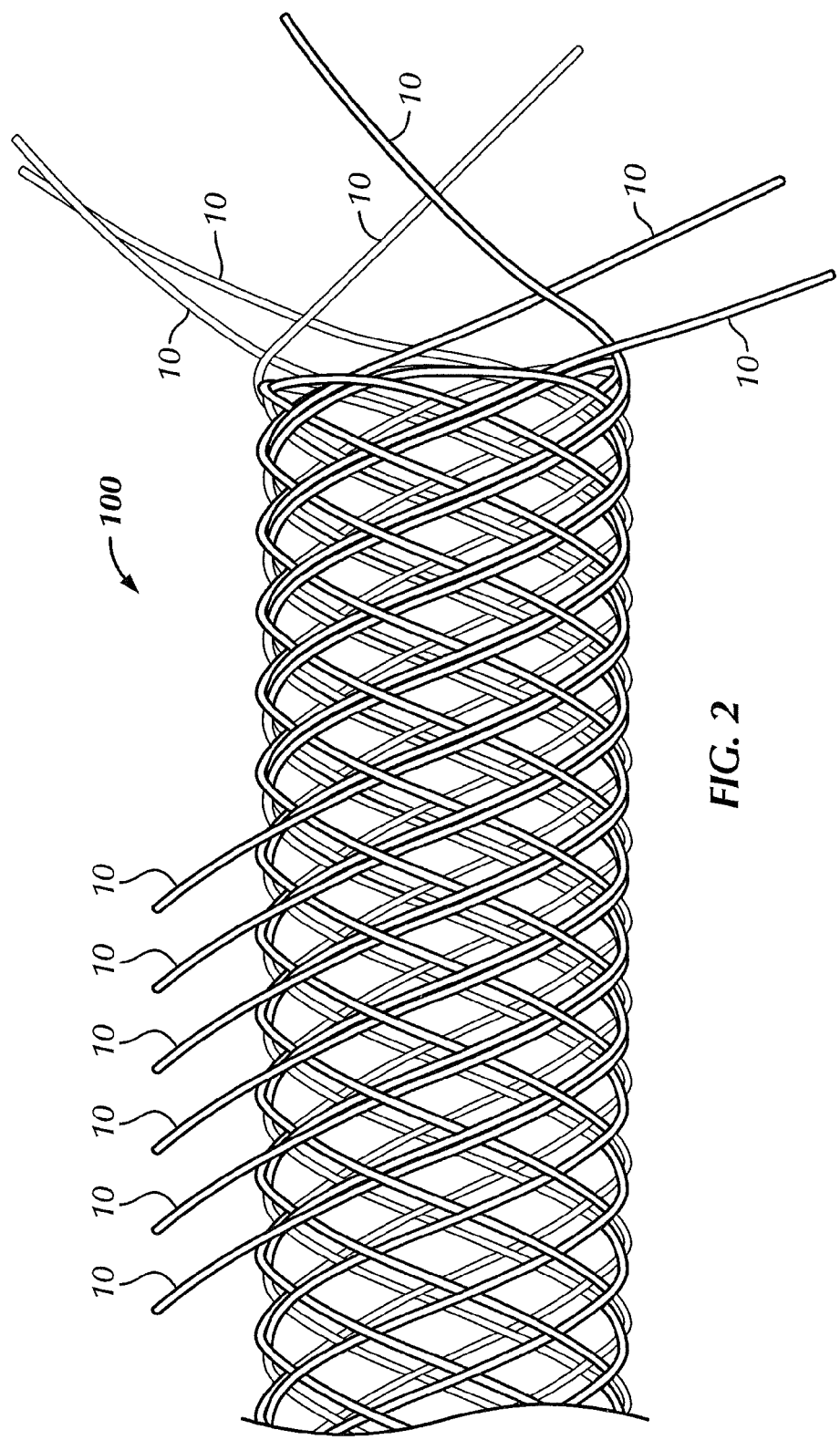
FIG. 2 shows an example of a portion of a device that is being configured for insertion into an anatomical structure, and at a stage of creation where half the free strand ends have been backbraided and the other half remain at one end of the device.

After this heat treatment, the device can be immediately quenched in deionized water until cool. Next, the free strand ends of the device can be backbraided as desired and then baked according to the information in the same table and immediately quenched in deionized water until cool. FIG. 2 shows device 100 after half of the twelve loose strand ends have been backbraided.

Figure 3:
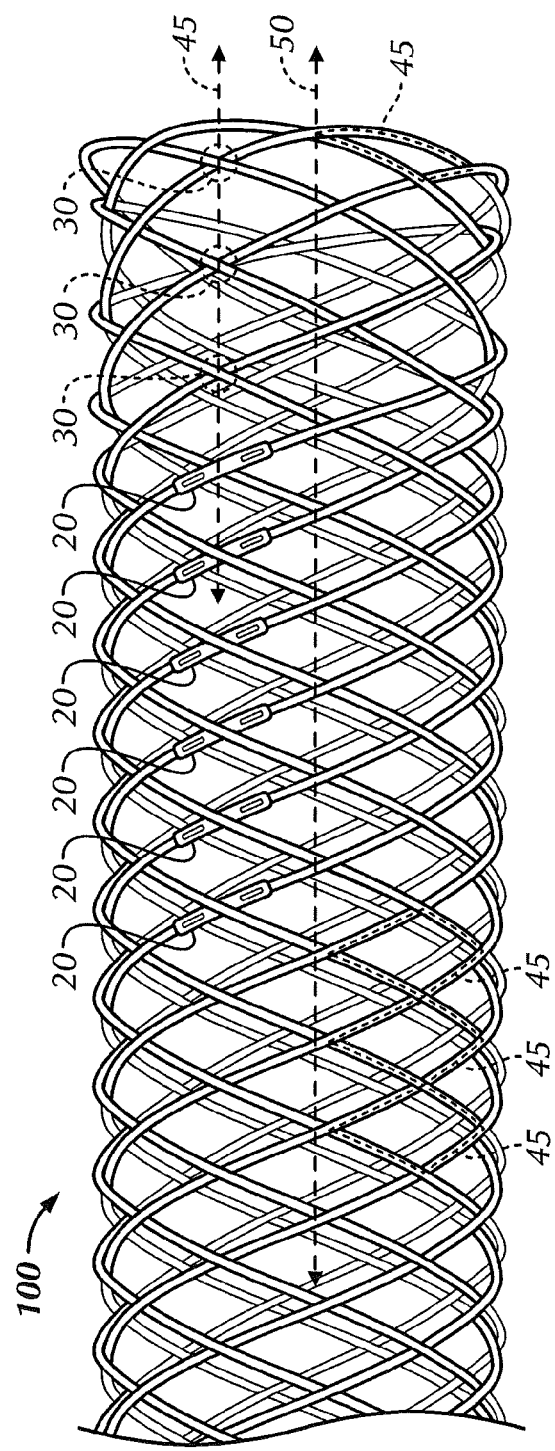
FIG. 3 shows an example of a portion of a device after the weaving reflected in FIG. 1 and the backbraiding reflected in FIG. 2 and that includes coupling structures equal in number to the strands used to create it. Specifically, one coupling structure has been laser welded to each of six different pairs of substantially-aligned strand end portions of the device (for a total of six coupling structures).

Next, one or more coupling structures (e.g., coupling structures that include nickel and titanium, such as 55.8 percent by weight of the total composition and titanium as the balance of the total composition) may be coupled to strand end portions of the woven device at any desired location along the length of the device. The device may be loaded onto a mandrel before the coupling structure(s) are positioned so that the internal diameter of the device is accurately set. Once the coupling structures have been positioned as desired, they can be secured to the strand end portions using any suitable technique, such as laser welding (which is described in more detail below). FIGS. 3-4B show examples of device 100 after coupling structures 20 have each been placed into contact with a pair of strand end portions and then welded to those strand end portions using laser welding as described below. FIG. 5, depicts the two device ends 102 and 104 of a version of device 100 created through the weaving, backbraiding, and coupling structure securing techniques that produced the devices shown in FIGS. 1-4B and 6-9, and shows that device ends 102 and 104 (device end 104 is the device end nearest the coupling structures that were used) are each defined by strand bends 40 (not all of which are labeled) that all have a substantially similar shape.

Figure 4A:
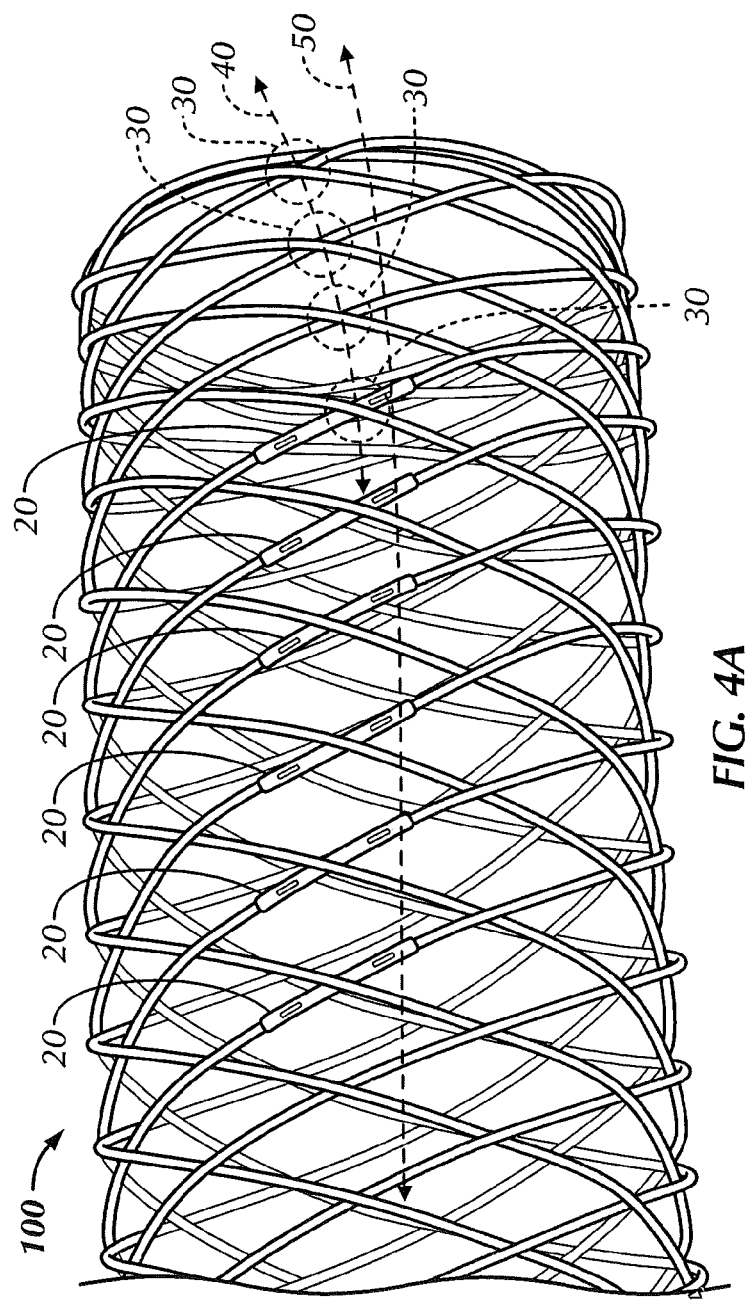
FIGS. 4A and 4B show examples of portions of other devices similar to the one shown in FIG. 3.
Figure 4B:
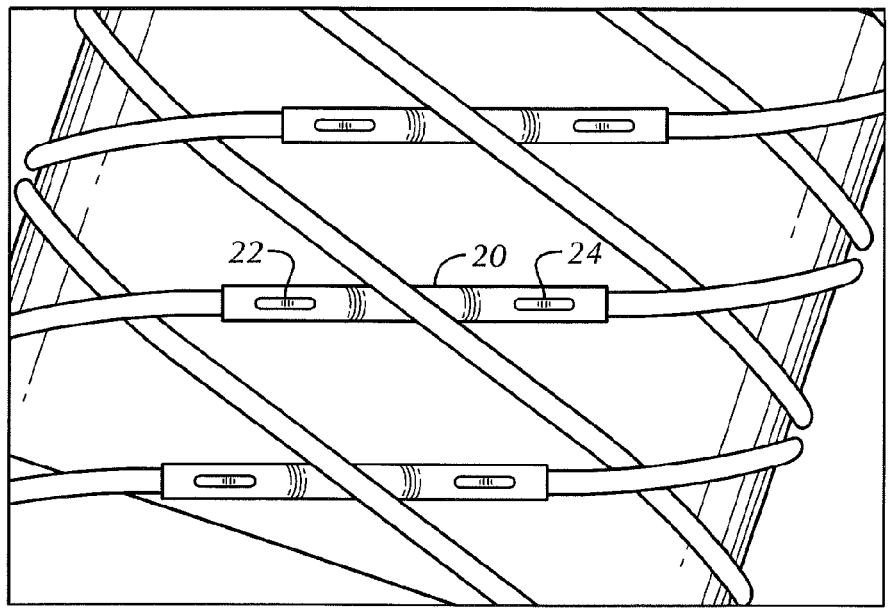
Figure 5:
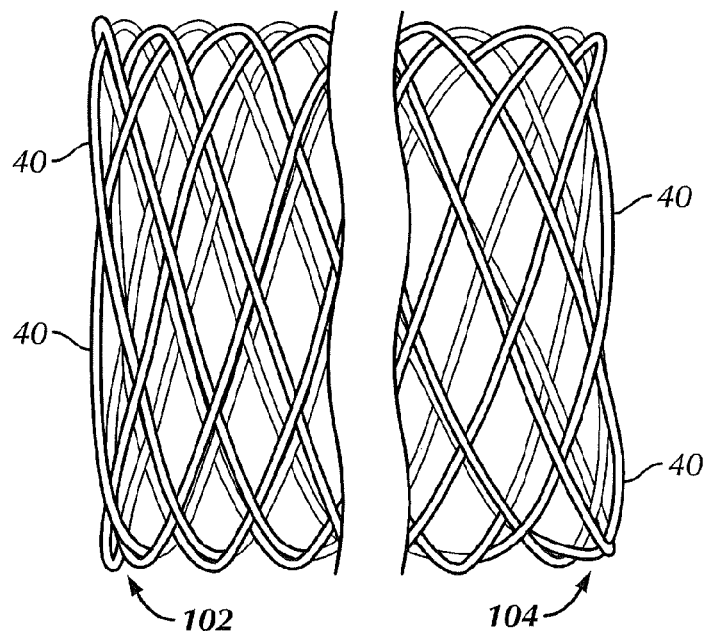
FIG. 5 shows the configuration of the device ends (and the similarity of the strand bends that define them) of a device similar to the one shown in FIGS. 3 and 4.

As shown in FIGS. 3 and 4A, in some embodiments, the coupling structure nearest to a particular device end (e.g., the right-most coupling structure 20 shown in these figures) may be spaced apart from that device end by at least one strand crossing or more. In the embodiment shown in these figures, the right-most coupling structure 20 that is depicted is spaced apart from the depicted device end by at least three strand crossings (which are designated by a circle marked 30) taken along a line 40 that is substantially parallel to longitudinal axis 50 of device 10. This right-most coupling structure is spaced apart from the depicted device end by at least one device opening or more; in particular, by at least three device openings (device openings 45 have been outlined elsewhere in the figure to show that such openings (also characterizable as mesh openings) are defined by strand crossings and, in particular, four strand crossings except for the end-most rows of device openings, which are defined by only three strand crossings (thus, all the device openings of the version of device 100 shown in this figure are defined by at least three strand crossings)). Furthermore, this right-most coupling structure forms the fourth strand crossing 30 along line 40 from the depicted device end, and is positioned beneath a strand of device 10 that crosses over it. Each of the other coupling structures 20 is likewise positioned beneath a strand of device 10 that crosses over it. Prior to the securing, the strand ends to which a given coupling structure is secured may be cut (as necessary) so as to be substantially centered beneath the strand that will pass over that coupling structure; consequently, the coupling structure will be substantially centered at the crossing it, in part, defines, as is true of the coupling structures 20 shown in FIGS. 3-4B.

Figure 6:
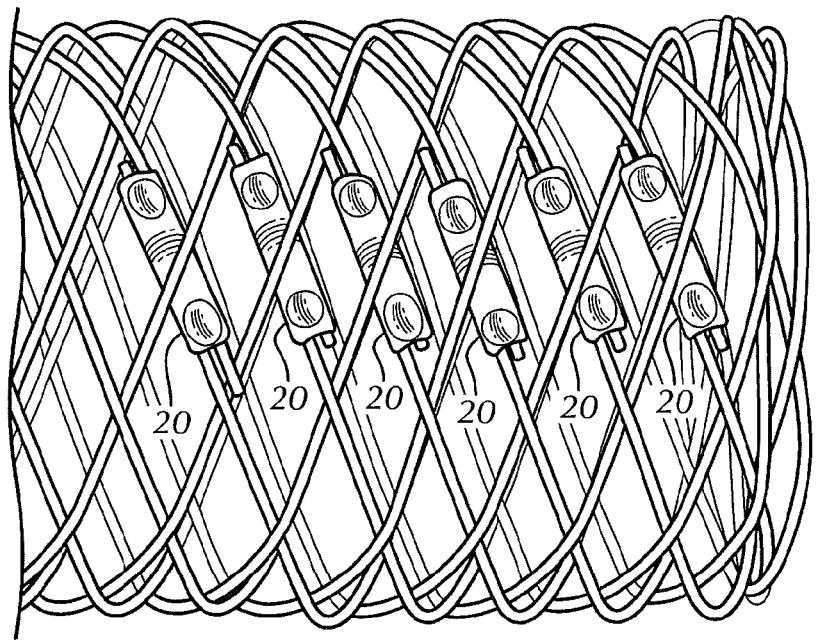
FIG. 6 shows an example of a portion of a device having coupling structures that are axially-aligned and that secure two strand end portions each in overlapping relationship.
Figure 7:
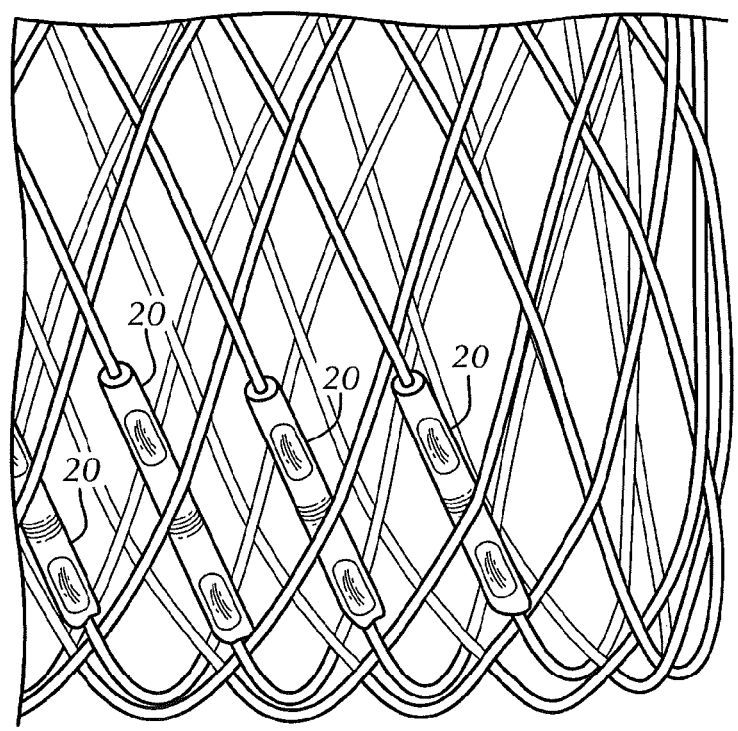
FIG. 7 shows an example of a portion of a device having coupling structures that are axially-aligned and that secure two substantially-aligned strand end portions each.
Figure 8:
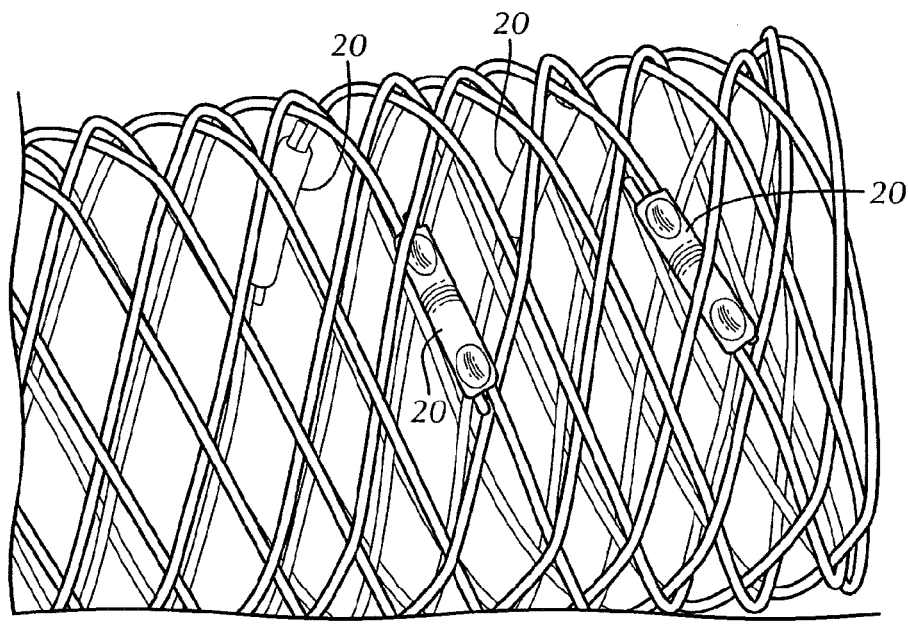
FIG. 8 shows an example of a portion of a device similar to the one shown in FIG. 6, except that adjacent coupling structures are spaced apart from each other around the circumference of the device. Two of the coupling structures that are farthest from the viewer are labeled.
Figure 9:
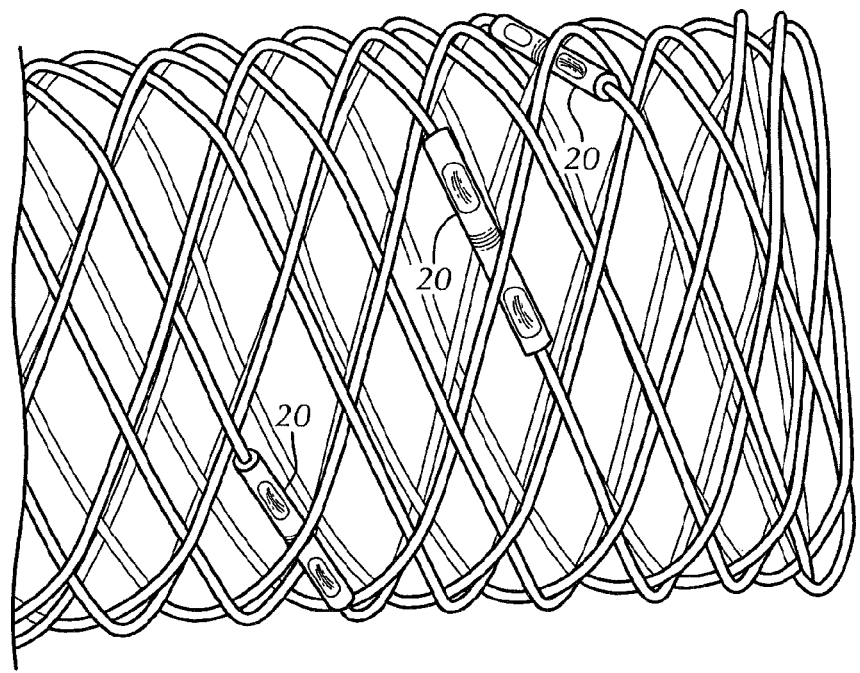
FIG. 9 shows an example of a portion of a device similar to the one shown in FIG. 7, except that adjacent coupling structures are spaced apart from each other around the circumference of the device.

The coupling structures that are used (for stents, the number of coupling structures will preferably equal the number of strands) may be axially aligned as are coupling structures 20 shown in FIGS. 3, 4A, and 4B and in FIGS. 6 and 7, or they may be spaced apart from each other axially and positioned around the circumference of the device, as are coupling structures 20 shown in FIGS. 8 and 9. The cutter used to cut the strand ends may be an Erem® cutter Model 576TX (carbide cutter) or 503ETST (oblique head carbide cutter), which are available from Cooper Hand Tools (Cooper Industries, LLC). Given the small size of the device, a microscope may be employed during the strand end cutting and coupling structure placement.

Figure 10A:
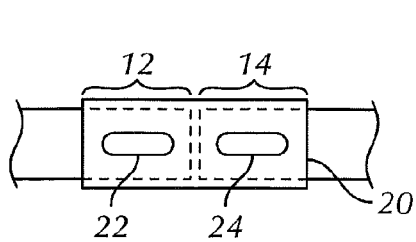
FIG. 10A depicts one coupling structure secured to two strand end portions that are substantially aligned.
Figure 10B:
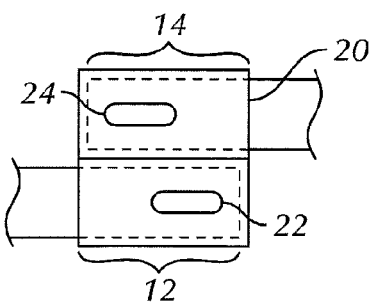
FIG. 10B depicts one coupling structure secured to two strand end portions that overlap with each other.
Figure 10C:
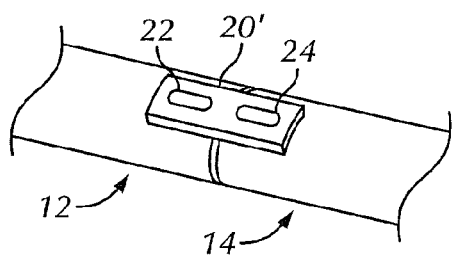
FIG. 10C depicts another embodiment of a coupling structure that is secured to two strand end portions that are substantially aligned.

Examples of coupling structures for joining or coupling two strand ends, which can be of different strands or the same strand, and example arrangements of strand end portions secured by them are shown in FIGS. 10A-10C. FIG. 10A shows coupling structure 20 secured to strand end portions 12 and 14 in a butt joint or butt configuration; as a result of this arrangement, strand end portions 12 and 14 are substantially aligned with each other. Coupling structure 20 is secured to strand end portion 12 by a weld that forms a first welded region 22 and to strand end portion 14 by a weld that forms a second welded region 24. As shown, first welded region 22 is not connected to second welded region 24 by another welded region; the two welded regions are spaced apart from each and separate. Furthermore, the two strand end portions shown in this figure are not in direct contact with each other (there is a slight gap between their ends), though in other embodiments they are in direct contact with each other. The version of coupling structure 20 shown in FIG. 10A has a passageway that exists prior to the coupling structure being secured to either of the strand end portions, and the passageway is sized to receive one device strand.

FIG. 10B shows coupling structure 20 secured to strand end portions 12 and 14 in lap joint or lap configuration; this configuration also may be characterized as overlapping. As a result, the two strand end portions are positioned beside each other rather than end-to-end. Though there is a small gap shown between them in this embodiment, in other embodiments there is direct side-to-side contact between them. The two welded regions 22 and 24 share the same characteristics as those in the FIG. 10A embodiment: they are not connected to each other by another welded region; they are spaced apart from each and separate. Although the welds that produced the two welded regions illustrated schematically in FIG. 10B are directed to only one strand end portion, each, they could both also be applied to both strand end portions, as were the welds that produced the welded regions shown in, for example, FIG. 6. The version of coupling structure 20 shown in FIG. 10B has a passageway that exists prior to the coupling structure being secured to either of the strand end portions, and the passageway is sized to receive two device strands.

FIG. 10C shows another embodiment of one of the present coupling structures, coupling structure 20', which is secured to first strand end portion 12 and to second strand end portion 14 by two welds that form first and second welded regions 22 and 24. Coupling structure 20' does not have a passageway; instead, it is configured as a portion of a tubular structure (e.g., as a strip with an arc, though in other embodiments the strip is flat).

Figure 11A:
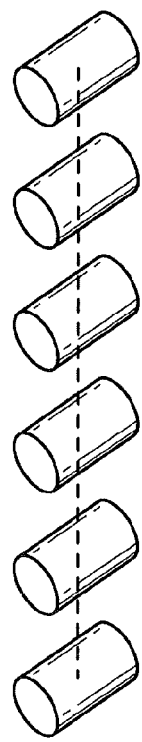
FIGS. 11A and 11B are schematic representations showing different example arrangements of coupling structures for a device such as a woven stent.
Figure 11B:
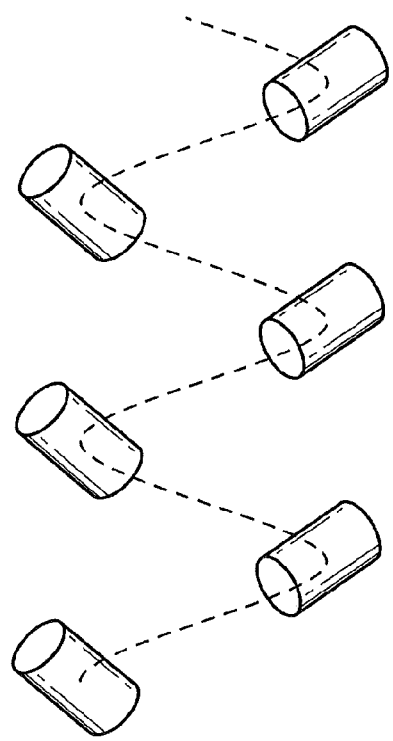

FIG. 11A is a schematic representation showing that the coupling structures 20 for a given device can be axially aligned. FIG. 11B shows they can be helically arranged, which is one way of offsetting them axially and circumferentially (such as at 60 degree intervals) from each other.

Figure 12:
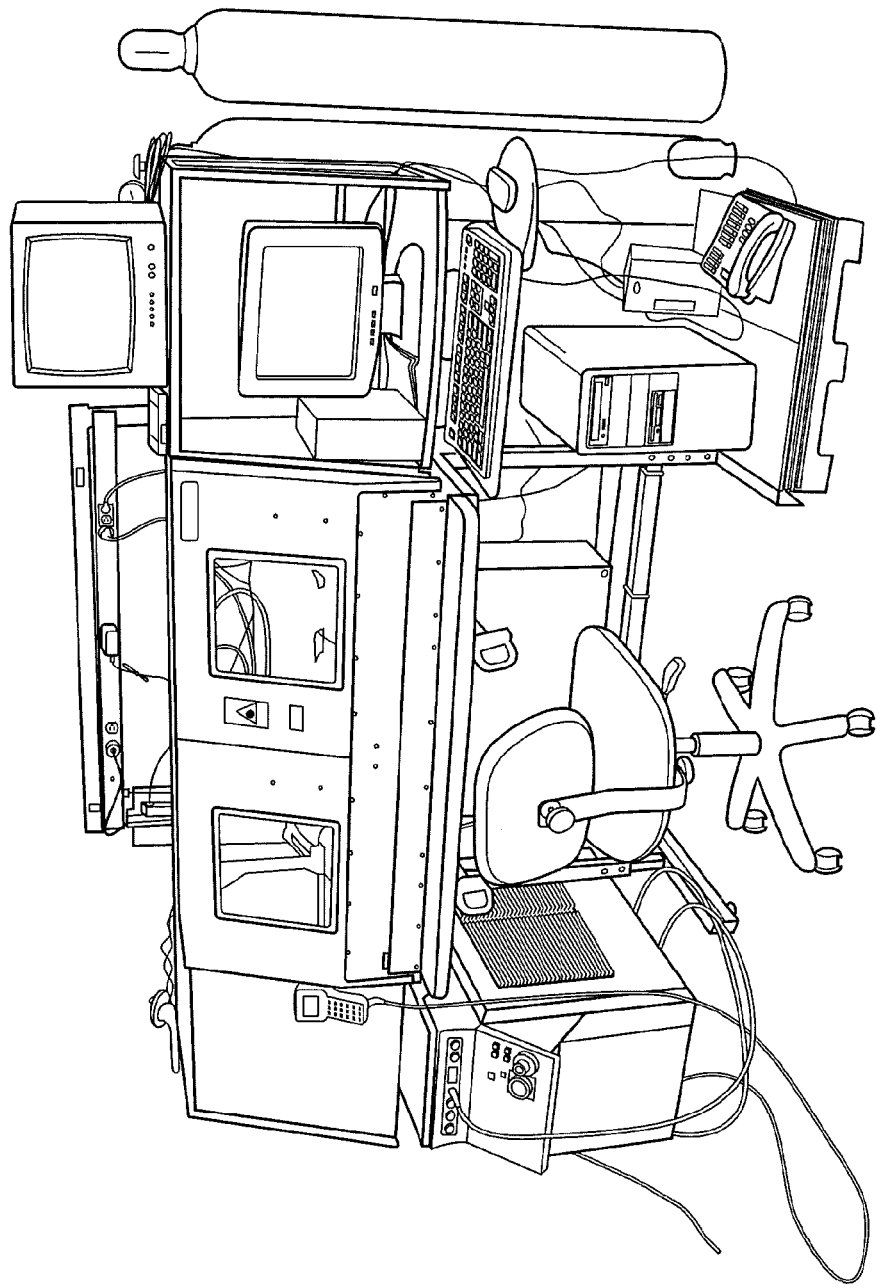
FIG. 12 shows an example of a laser welding system that can be used to create the devices shown in FIGS. 2-9.

For woven stents made from nitinol wires (such as those that include 56.0 percent nickel by weight of the total composition and titanium as the balance of the total composition), coupling structures made from the same type of nitinol (such as 55.8 percent nickel by weight of the total composition and titanium as the balance of the total composition) can be used to couple the ends of different strands using laser welding, such as pulsed laser welding. An example of a suitable laser welding system is shown in FIG. 12, and includes a LASAG pulsed Nd:YAG (Neodymium: Yttrium Aluminum Garnet) "EasyWelder" laser system from the SLS 200 series (Lasag, Switzerland).

Figures 13, 14A:
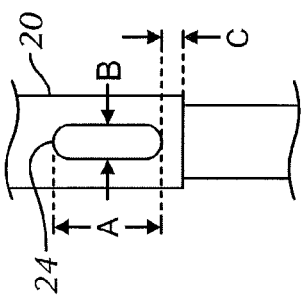
FIG. 13 is a table providing example inner diameter, outer diameter and length dimensions of nitinol coupling structures that can be used for a given diameter nitinol wire size of a given size of six-strand woven stent, and further provides example settings for the LASAG welding system identified below (scfh stands for cubic feet per hour under standard conditions).
FIG. 14A is a detail view showing certain dimensions of a welded region created by a weld that secures the depicted coupling structure to the depicted strand.

For a stent made from six nitinol wires (nickel—56.0 percent by weight of the total composition; titanium—balance of the total composition), six nitinol coupling structures (nickel—55.8 percent by weight of the total composition; titanium—balance of the total composition) may be used. The table in FIG. 13 provides example inner diameter, outer diameter and length dimensions of nitinol coupling structures that can be used for a given diameter nitinol wire size of a given size of six-strand woven stent, and further provides example settings for the LASAG welding system identified above (scfh stands for cubic feet per hour under standard conditions).

The following is a brief description of how coupling structures are secured to the pairs of wire end portions of a heat-treated (according to the technique described above), six-wire woven nitinol stent through a process that is at least partially automated (and in other embodiments fully automated) using the LASAG welding system described above:

the stent has been partially braided back (e.g., by hand), meaning that six of the 12 wire ends are braided back into the stent;

starting at any suitable wire crossing (e.g., the fourth or fifth wire crossing from the end that has been braided back), the wire ends are cut as described above such that the ends of the wires come into contact under the crossing wire;

the coupling structures are loaded onto the wire ends and centered about the crossing wire while on a mandrel so that the internal diameter of the stent is accurately set;

the coupling region of the stent is secured to the mandrel with a spring loaded clip to prevent relative motion between the stent and mandrel, to accurately set the internal diameter of the stent, and to maintain the proper placement of the wire end portions within the coupling structures;

the mandrel mounted and secured stent is then placed in the laser welding system and the first coupling structure is aligned with the horizontal crosshair on the view screen of the system;

the welding program for the size of stent to be welded (examples provided below) is invoked; and the operator is prompted to align the crosshairs with the upper-left corner of the coupling. Once aligned, the operator presses the start button and the left weld bead is created. The system then moves and prompts the operator to align the crosshairs to the upper-right corner. Once aligned, the operator presses the start button and the right weld bead is created. The system then moves to the upper-left corner of the second coupling and the process is repeated. This continues until all 12 welds are completed.

Dimensions for welded region 24 of a given coupling structure 20 of one of the present devices (specifically, a woven stent such as those shown in FIGS. 1-4B) are depicted in FIG. 14A and example values for those dimensions are set forth in FIG. 14B. Table 2 below provides example values for the dimensions of a tubular coupling structure corresponding to the "Coupling Structure Code" set forth in FIG. 14B:

TABLE 2

| Coupling Structure Code | Coupling Structure Inner Dia. (in.) | Coupling Structure Outer Dia. (in.) | Coupling Structure Length (in.) |
|---|---|---|---|
| −01 | 0.0070 | 0.0100 | 0.070 |
| −02 | 0.0070 | 0.0100 | 0.080 |
| −03 | 0.0075 | 0.0105 | 0.100 |
| −04 | 0.0085 | 0.0120 | 0.120 |
| −05 | 0.0085 | 0.0120 | 0.150 |

Unless otherwise set forth, the tolerances for the values in FIG. 14B are as follows: X.=±1; .X=±0.5; .XX=±0.25; .XXX=±0.125. Unless otherwise set forth, the tolerances for the values in Table 2 are as follows: .X=±0.030; .XX=±0.010; .XXX=±0.005.

Thus, taking the first row of FIG. 14B as an example, a given stent with an internal diameter of 4.0 mm and a length of 40 mm made from nitinol wires (such as those described above) having 0.006 inch diameters could be made with tubular coupling structures (code −01) that each have an internal diameter of 0.0070 inches, an outer diameter of 0.0100 inches, and a length of 0.070 inches, with dimensions A, B, and C of the welded region produced by a laser weld that secures that coupling structure to one of the specified wires having the dimensions of A=0.010 inches, B=0.005 inches, and C=0.010 inches.

The following routines written in industry-standard NC (numerical code) can be used to program the LASAG welding system identified above for use in creating butt-coupled joints using the coupling structures described above for the various sizes of nitinol stents (formed from using the nickel-titanium mixture described above) recited before each routine:

| 4 mm ID stent |
|---|

```
;4 mm Stent Welding Program
M61                ;Laser Remote Control
; Welding Parameters
C101 Q10           ;FREQUENCY 10 HZ
C102 Q0.25         ;PULSE LENGTH 0.25 ms
C108 Q200          ;Peak Power 200 W
C111 Q120          ;A-Scale 120
M51                ;MONITOR LASER OK
;Move Laser to common work place
G90                ; Absolute Coordinate
F50                ; Feed Rate
X3.93 Y-4.6        ; Locate fixture and part
Z-2.656               ; Adjust Focus
; Weld six couplings
M26 H152           ; Reset Door
M98 P2                ; Goto Subroutine 1-1st Coupling
F4                 ; Fast Feed for inter move
X-.040 Y.037       ; Move back to relative 0,0
M98 P2                ; Goto Subroutine 1-2nd Coupling
F4                 ; Fast Feed for inter move
X-.040 Y.037       ; Move back to relative 0,0
M98 P2                ; Goto Subroutine 1-3rd Coupling
F4                 ; Fast Feed for inter move
X-.040 Y.037       ; Move back to relative 0,0
M98 P2                ; Goto Subroutine 1-4th Coupling
F4                 ; Fast Feed for inter move
X-.040 Y.037       ; Move back to relative 0,0
M98 P2                ; Goto Subroutine 1-5th Coupling
F4                 ; Fast Feed for inter move
X-.040 Y.037       ; Move back to relative 0,0
M98 P2                ; Goto Subroutine 1-6th Coupling
```

```
;Go Back to common work place
G90                     ; Absolute Coordinate
F50                     ; Feed Rate
X3.93 Y-4.6             ; Locate fixture and part
M25                     ; Open Door
M02                     ; End of NC
; /*------ End of Program ------*/
; Coupling Weld Subroutine
O2                      ; Welding Routine
F1                      ; Feed Rate
G05Q1                   ; Jog with Pause/Move to Upper Left Corner
G91                     ; Incremental Coordinates
M8                      ; Gas On
G4F.5                   ; Dwell for .5 seconds
X0.008 Y-.004               ; Offset from corner of coupling
M71                     ; Laser Processing with Sync. feed
X0.015                  ; Weld left bead = .015:
M70                     ; Stop laser processing
X0.058 Y.0045               ; Index to Right Upper Corner
G05Q1                   ; Jog with Pause/Adjust to Upper Right Corner
X-0.008 Y-.004              ; Offset from right corner of coupling
M71                     ; Laser Processing with Sync. feed
X-0.015                 ; Weld bead = .015:
M70                     ; Stop laser processing
M9                      ; Gas off
M99                     ; Return
                5 mm ID stent ;5 mm Stent Welding Program
M61                     ;Laser Remote Control
; Welding Parameters
C101 Q10                ;FREQUENCY 10 HZ
C102 Q0.25              ;PULSE LENGTH 0.25 ms
C108 Q200               ;Peak Power 200W
C111 Q120               ; A-Scale 120
M51                     ;MONITOR LASER OK
; Move to common work place
G90                     ; Absolute Coordinate
F50                     ; Feed Rate
X3.93 Y-4.6             ; Locate fixture and part
Z-2.656                 ; Adjust Focus
; Weld six couplings
M26 H152                ; Reset Door
M98 P2                      ; Goto Subroutine 1-1st Coupling
F4                      ; Fast Feed for inter move
X-.040 Y.041            ; Move back to relative 0,0
M98 P2                      ; Goto Subroutine 1-2nd Coupling
F4                      ; Fast Feed for inter move
X-.040 Y.041            ; Move back to relative 0,0
M98 P2                      ; Goto Subroutine 1-3rd Coupling
F4                      ; Fast Feed for inter move
X-.040 Y.041            ; Move back to relative 0,0
M98 P2                      ; Goto Subroutine 1-4th Coupling
F4                      ; Fast Feed for inter move
X-.040 Y.041            ; Move back to relative 0,0
M98 P2                      ; Goto Subroutine 1-5th Coupling
F4                      ; Fast Feed for inter move
X-.040 Y.041            ; Move back to relative 0,0
M98 P2                      ; Goto Subroutine 1-6th Coupling
;Go Back to common work place
G90                     ; Absolute Coordinate
F50                     ; Feed Rate
X3.93 Y-4.6             ; Locate fixture and part
M25 H152                ; Open Door
M02                     ; End of NC
; Coupling Weld Subroutine
O2                      ; Welding Routine
F1                      ; Feed Rate
G05Q1                   ; Jog with Pause/Move to Upper Left Corner
G91                     ; Incremental Coordinates
M8                      ; Gas On
G4F.5                   ; Dwell for .5 seconds
X0.010 Y-.004               ; Offset from corner of coupling
M71                     ; Laser Processing with Sync. feed
X0.015                  ; Weld left bead = .015:
M70                     ; Stop laser processing
X0.055 Y.0045               ; Index to Right Upper Corner
G05Q1                   ; Jog with Pause/Adjust to Upper Right Corner
X-0.010 Y-.004              ; Offset from right corner of coupling
M71                     ; Laser Processing with Sync. feed
X-0.015                 ; Weld bead = .015:
M70                     ; Stop laser processing
M9                      ; Gas off
M99                     ; Return
                6 mm ID stent ;6 mm Stent Welding Program
M61                     ;Laser Remote Control
; Welding Parameters
C101 Q10                ;FREQUENCY 10 HZ
C102 Q0.3               ;PULSE LENGTH 0.3 ms
C108 Q300               ;Peak Power 200W
C111 Q100               ;A-Scale 100
M51                     ;MONITOR LASER OK
; Move to common work place
G90                     ; Absolute Coordinate
F50                     ; Feed Rate
X3.93 Y-4.6             ; Locate fixture and part
Z-2.6716                ; Adjust Focus
; Weld six couplings
M26 H152                ; Reset Door
M98 P2                      ; Goto Subroutine 1-1st Coupling
F4                      ; Fast Feed for inter move
X-.060 Y.045            ; Move back to relative 0,0
M98 P2                      ; Goto Subroutine 1-2nd Coupling
F4                      ; Fast Feed for inter move
X-.060 Y.045            ; Move back to relative 0,0
M98 P2                      ; Goto Subroutine 1-3rd Coupling
F4                      ; Fast Feed for inter move
X-.060 Y.045            ; Move back to relative 0,0
M98 P2                      ; Goto Subroutine 1-4th Coupling
F4                      ; Fast Feed for inter move
X-.060 Y.045            ; Move back to relative 0,0
M98 P2                      ; Goto Subroutine 1-5th Coupling
F4                      ; Fast Feed for inter move
X-.060 Y.045            ; Move back to relative 0,0
M98 P2                      ; Goto Subroutine 1-6th Coupling
; Go Back to Common work place
G90                     ; Absolute Coordinate
F50                     ; Feed Rate
X3.93 Y-4.6             ; Locate fixture and part
M25 H152                ; Open Door
M02                     ; End of NC
; Coupling Weld Subroutine
O2                      ; Welding Routine
F1                      ; Feed Rate
G05Q1                   ; Jog with Pause/Move to Upper Left Corner
G91                     ; Incremental Coordinates
M8                      ; Gas On
G4F.5                   ; Dwell for .5 seconds
X0.010 Y-.005               ; Offset from corner of coupling
M71                     ; Laser Processing with Sync. feed
X0.015                  ; Weld left bead = .015:
M70                     ; Stop laser processing
X0.075 Y.005            ; Index to Right Upper Corner
G05Q1                   ; Jog with Pause/Adjust to Upper Right Corner
X-0.010 Y-.005              ; Offset from right corner of coupling
M71                     ; Laser Processing with Sync. feed
X-0.015                 ; Weld bead = .015:
M70                     ; Stop laser processing
M9                      ; Gas off
M99                     ; Return
                7 mm ID stent ;7 mm Stent Welding Program
M61                     ;Laser Remote Control
; Welding Parameters
C101 Q10                ;FREQUENCY 10 HZ
C102 Q0.3               ;PULSE LENGTH 0.3 ms
C108 Q300               ;Peak Power 200W
C111 Q100               ;A-Scale 100
M51                     ;MONITOR LASER OK
; Move to common work place
G90                     ; Absolute Coordinate
F50                     ; Feed Rate
X3.93 Y-4.6             ; Locate fixture and part
Z-2.6716                ; Adjust Focus
; Weld six couplings
```

```
M26 H152            ; Reset Door
M98 P2                      ; Goto Subroutine 1-1st Coupling
F4                  ; Fast Feed for inter move
X-.060 Y.049        ; Move back to relative 0,0
M98 P2                      ; Goto Subroutine 1-2nd Coupling
F4                  ; Fast Feed for inter move
X-.060 Y.049        ; Move back to relative 0,0
M98 P2                      ; Goto Subroutine 1-3rd Coupling
F4                  ; Fast Feed for inter move
X-.060 Y.049        ; Move back to relative 0,0
M98 P2                      ; Goto Subroutine 1-4th Coupling
F4                  ; Fast Feed for inter move
X-.060 Y.049        ; Move back to relative 0,0
M98 P2                      ; Goto Subroutine 1-5th Coupling
F4                  ; Fast Feed for inter move
X-.060 Y.049        ; Move back to relative 0,0
M98 P2                      ; Goto Subroutine 1-6th Coupling
; Go Back to Common Work Place
G90                 ; Absolute Coordinate
F50                 ; Feed Rate
X3.93 Y-4.6         ; Locate fixture and part
M25 H152            ; Open Door
M02                 ; End of NC
; Coupling Weld Subroutine
O2                  ; Welding Routine
F1                  ; Feed Rate
G05Q1                       ; Jog with Pause/Move to Upper Left Corner
G91                 ; Incremental Coordinates
M8                  ; Gas On
G4F.5               ; Dwell for .5 seconds
X0.010 Y-.005               ; Offset from corner of coupling
M71                 ; Laser Processing with Sync. feed
X0.015                      ; Weld left bead = .015:
M70                 ; Stop laser processing
X0.075 Y.005                ; Index to Right Upper Corner
G05Q1                       ; Jog with Pause/Adjust to Upper Right Corner
X-0.010 Y-.005              ; Offset from right corner of coupling
M71                 ; Laser Processing with Sync. feed
X-0.015                     ; Weld bead = .015:
M70                 ; Stop laser processing
M9                  ; Gas off
M99                 ; Return
                            8 mm ID stent ;8 mm Stent Welding Program
M61                 ;Laser Remote Control
; Welding Parameters
C101 Q10            ;FREQUENCY 10 HZ
C102 Q0.3           ;PULSE LENGTH 0.3 ms
C108 Q300           ;Peak Power 200W
C111 Q100           ; A-Scale 100
M51                 ;MONITOR LASER OK
; Move to common work place
G90                 ; Absolute Coordinate
F50                 ; Feed Rate
X3.93 Y-4.6         ; Locate fixture and part
Z-2.6544            ; Adjust Focus
; Weld six Couplings
M26 H152            ; Reset Door
M98 P2                      ; Goto Subroutine 1-1st Coupling
F4                  ; Fast Feed for inter move
X-.067 Y.053        ; Move back to relative 0,0
M98 P2                      ; Goto Subroutine 1-2nd Coupling
F4                  ; Fast Feed for inter move
X-.067 Y.053        ; Move back to relative 0,0
M98 P2                      ; Goto Subroutine 1-3rd Coupling
F4                  ; Fast Feed for inter move
X-.067 Y.053        ; Move back to relative 0,0
M98 P2                      ; Goto Subroutine 1-4th Coupling
F4                  ; Fast Feed for inter move
X-.067 Y.053        ; Move back to relative 0,0
M98 P2                      ; Goto Subroutine 1-5th Coupling
F4                  ; Fast Feed for inter move
X-.067 Y.053        ; Move back to relative 0,0
M98 P2                      ; Goto Subroutine 1-6th Coupling
; Go Back to Common Work Place
G90                 ; Absolute Coordinate
F50                 ; Feed Rate
X3.93 Y-4.6         ; Locate fixture and part
M25 H152            ; Open Door
M02                 ; End of NC
; Coupling Weld Subroutine
O2                  ; Welding Routine
F1                  ; Feed Rate
G05Q1                       ; Jog with Pause/Move to Upper Left Corner
G91                 ; Incremental Coordinates
M8                  ; Gas On
G4F.5               ; Dwell for .5 seconds
X0.010 Y-.006               ; Offset from corner of coupling
M71                 ; Laser Processing with Sync. feed
X0.015                      ; Weld left bead = .015:
M70                 ; Stop laser processing
X0.095 Y.006                ; Index to Right Upper Corner
G05Q1                       ; Jog with Pause/Adjust to Upper Right Corner
X-0.010 Y-.006              ; Offset from right corner of coupling
M71                 ; Laser Processing with Sync. feed
X-0.015                     ; Weld bead = .015:
M70                 ; Stop laser processing
M9                  ; Gas off
M99                 ; Return
                            9 mm ID stent ;9 mm Stent Welding Program
M61                 ;Laser Remote Control
; Welding Parameters
C101 Q10            ;FREQUENCY 10 HZ
C102 Q0.3           ;PULSE LENGTH 0.3 ms
C108 Q300           ;Peak Power 200 W
C111 Q100           ; A-Scale 100
M51                 ;MONITOR LASER OK
; Move to common work place
G90                 ; Absolute Coordinate
F50                 ; Feed Rate
X3.93 Y-4.6         ; Locate fixture and part
Z-2.6716            ; Adjust Focus
; Weld six Couplings
M26 H152            ; Reset Door
M98 P2                      ; Goto Subroutine 1-1st Coupling
F4                  ; Fast Feed for inter move
X-.067 Y.057        ; Move back to relative 0,0
M98 P2                      ; Goto Subroutine 1-2nd Coupling
F4                  ; Fast Feed for inter move
X-.067 Y.057        ; Move back to relative 0,0
M98 P2                      ; Goto Subroutine 1-3rd Coupling
F4                  ; Fast Feed for inter move
X-.067 Y.057        ; Move back to relative 0,0
M98 P2                      ; Goto Subroutine 1-4th Coupling
F4                  ; Fast Feed for inter move
X-.067 Y.057        ; Move back to relative 0,0
M98 P2                      ; Goto Subroutine 1-5th Coupling
F4                  ; Fast Feed for inter move
X-.067 Y.057        ; Move back to relative 0,0
M98 P2                      ; Goto Subroutine 1-6th Coupling
; Go Back to Common Work Place
G90                 ; Absolute Coordinate
F50                 ; Feed Rate
X3.93 Y-4.6         ; Locate fixture and part
M25 H152            ; Open Door
M02                 ; End of NC
; Coupling Weld Subroutine
O2                  ; Welding Routine
F1                  ; Feed Rate
G05Q1               ; Jog with Pause/Move to Upper Left Corner
G91                 ; Incremental Coordinates
M8                  ; Gas On
G4F.5               ; Dwell for .5 seconds
X0.010 Y-.006               ; Offset from corner of coupling
M71                 ; Laser Processing with Sync. feed
X0.015                      ; Weld left bead = .015:
M70                 ; Stop laser processing
X0.095 Y.006                ; Index to Right Upper Corner
G05Q1                       ; Jog with Pause/Adjust to Upper Right Corner
X-0.010 Y-.006              ; Offset from right corner of coupling
M71                 ; Laser Processing with Sync. feed
X-0.015                     ; Weld bead = .015:
M70                 ; Stop laser processing
M9                  ; Gas off
M99                 ; Return
```

-continued

| 10 mm ID stent | |
|---|---|
| ;10 mm Stent Welding Program | |
| M61 | ;Laser Remote Control |
| ; Welding Parameters | |
| C101 Q10 | ;FREQUENCY 10 HZ |
| C102 Q0.3 | ;PULSE LENGTH 0.3 ms |
| C108 Q300 | ;Peak Power 200 W |
| C111 Q100 | ; A-Scale 100 |
| M51 | ;MONITOR LASER OK |
| ; Move to common work place | |
| G90 | ; Absolute Coordinate |
| F50 | ; Feed Rate |
| X3.93 Y-4.6 | ; Locate fixture and part |
| Z-2.6716 | ; Adjust Focus |
| ; Weld six Couplings | |
| M26 H152 | ; Reset Door |
| M98 P2 | ; Goto Subroutine 1-1st Coupling |
| F4 | ; Fast Feed for inter move |
| X-.067 Y.061 | ; Move back to relative 0,0 |
| M98 P2 | ; Goto Subroutine 1-2nd Coupling |
| F4 | ; Fast Feed for inter move |
| X-.067 Y.061 | ; Move back to relative 0,0 |
| M98 P2 | ; Goto Subroutine 1-3rd Coupling |
| F4 | ; Fast Feed for inter move |
| X-.067 Y.061 | ; Move back to relative 0,0 |
| M98 P2 | ; Goto Subroutine 1-4th Coupling |
| F4 | ; Fast Feed for inter move |
| X-.067 Y.061 | ; Move back to relative 0,0 |
| M98 P2 | ; Goto Subroutine 1-5th Coupling |
| F4 | ; Fast Feed for inter move |
| X-.067 Y.061 | ; Move back to relative 0,0 |
| M98 P2 | ; Goto Subroutine 1-6th Coupling |
| ; Go Back to Common Work Place | |
| G90 | ; Absolute Coordinate |
| F50 | ; Feed Rate |
| X3.93 Y-4.6 | ; Locate fixture and part |
| M25 H152 | ; Open Door |
| M02 | ; End of NC |
| ; Coupling Weld Subroutine | |
| O2 | ; Welding Routine |
| F1 | ; Feed Rate |
| G05Q1 | ; Jog with Pause/Move to Upper Left Corner |
| G91 | ; Incremental Coordinates |
| M8 | ; Gas On |
| G4F.5 | ; Dwell for .5 seconds |
| X0.010 Y-.006 | ; Offset from corner of coupling |
| M71 | ; Laser Processing with Sync. feed |
| X0.015 | ; Weld left bead = .015: |
| M70 | ; Stop laser processing |
| X0.095 Y.006 | ; Index to Right Upper Corner |
| G05Q1 | ; Jog with Pause/Adjust to Upper Right Corner |
| X-0.010 Y-.006 | ; Offset from right corner of coupling |
| M71 | ; Laser Processing with Sync. feed |
| X-0.015 | ; Weld bead = .015: |
| M70 | ; Stop laser processing |
| M9 | ; Gas off |
| M99 | ; Return |

It should be understood that the present methods and the devices they produce are not intended to be limited to the particular forms disclosed. Rather, they are to cover all modifications, equivalents, and alternatives falling within the scope of the claims. For example, while the devices illustrated in the figures have been woven from multiple strands, in other embodiments, the present methods could be applied to devices woven or otherwise created from only a single strand of material (such as a nitinol wire). Further, while stents have been shown in the figures, other devices suited for placement in an anatomical structure, such as filters and occluders, could have their free strand ends joined according to the present methods.

The claims are not to be interpreted as including means-plus- or step-plus-function limitations, unless such a limitation is explicitly recited in a given claim using the phrase(s) "means for" or "step for," respectively.

What is claimed is:

1. A self-expanding stent comprising:
   a single strand including a strand portion on both sides of a strand bend, each of the strand portions having an end, the strand portions being woven in a first direction to form a tubular body, the strand portions being back braided in a second direction by at least two strand crossings,
   wherein the strand portion ends are secured together to form a joint assembly, the joint assembly being spaced apart from each end of the tubular body; and
   wherein a crossing strand portion crosses over the joint assembly at a position radially outward from the joint assembly.

2. The stent of claim 1, wherein the strand portion ends are secured together by welding.

3. The device of claim 1, wherein the strand portion ends are secured together by soldering.

4. The device of claim 1, wherein the strand portion ends are secured together by braising.

5. The stent of claim 1, wherein the strand portion ends are aligned end-to-end.

6. The stent of claim 1, wherein each of the strand portion ends is welded to a coupling structure.

7. The stent of claim 1, wherein the strands comprise Nitinol.

8. A device configured for insertion into an anatomical structure, the device comprising:
   one or more strands, each strand comprising a pair of strand end portions:
   a joint assembly comprising two different strand end portions;
   wherein the two different strand end portions include nickel and titanium, and
   wherein the joint assembly is positioned beneath one strand of the device that crosses over the joint assembly.

9. The device of claim 8, wherein the two different strand end portions are aligned end-to-end.

10. The device of claim 8, wherein the two different strand end portions are placed in a side-by-side relationship.

11. The device of claim 8, wherein the joint assembly is substantially centered beneath the one strand that crosses over that joint assembly.

12. The device of claim 8, wherein the one or more strands is one strand.

13. The device of claim 8, wherein the one or more strands are woven to form a self-expanding stent.

14. The device of claim 8, wherein the device comprises two or more device ends, wherein each device end is defined by strand bends, and the strand bends of all the device ends have a similar shape.

15. The device of claim 8, wherein the device comprises at least two device ends and a longitudinal axis, and wherein the joint assembly is nearer to one of the device ends than any other device end.

16. The device of claim 8, wherein the joint assembly is spaced apart from a nearest device end by at least one strand crossing.

17. The device of claim 8, wherein the joint assembly is spaced apart from a nearest device end by at least two strand crossings.

18. The device of claim 8, wherein the joint assembly is spaced apart from a nearest device end by at least three strand crossings.

19. The device of claim 8, wherein the joint assembly is spaced apart from a nearest device end by at least four strand crossings.

20. The device of claim 8, wherein the joint assembly is spaced apart from a nearest device end by at least five strand crossings.

21. The device of claim 8, wherein the joint assembly is formed by laser welding.

22. The device of claim 8, wherein the joint assembly is formed by electron beam welding.

23. The device of claim 8, wherein the joint assembly is formed by resistance welding.

24. The device of claim 8, wherein the joint assembly is formed by tungsten inert gas welding.

25. The device of claim 8, wherein the joint assembly is formed by metal inert gas welding.

26. The device of claim 8, wherein the joint assembly is formed by crimping.

27. The device of claim 8, wherein the joint assembly is formed by soldering.

28. The device of claim 8, wherein the joint assembly is formed by braising.

29. The device of claim 8, wherein the joint assembly is formed by gluing.

30. The device of claim 8, wherein the joint assembly comprises a coupling structure secured to the two different strand end portions, and wherein the coupling structure is not a strand of the device.

31. The device of claim 30, where the coupling structure is laser welded to a first strand end portion.

32. The device of claim 31, wherein the coupling structure is laser welded to the second strand end portion.

33. The device of claim 30, wherein the coupling structure is secured to the two different strand end portions by welding and the same weld is applied to both strand end portions.

34. The device of claim 8, wherein the two strand end portions directly touch each other.

35. The device of claim 8, wherein neither the strand end portions nor the joint assembly is smoothed after being secured.

36. The device of claim 8, wherein the joint assembly has a first length, wherein the device has a second length, and wherein the first length of the joint assembly is less than 15 percent of the second length of the device.

37. The device of claim 36, wherein the first length of the joint assembly is less than 2 percent of the second length of the device.

* * * * *